US011058803B2

(12) United States Patent
Smith et al.

(10) Patent No.: US 11,058,803 B2
(45) Date of Patent: *Jul. 13, 2021

(54) MEDICAL DEVICES AND IMPLEMENTS WITH LIQUID-IMPREGNATED SURFACES

(71) Applicant: Massachusetts Institute of Technology, Cambridge, MA (US)

(72) Inventors: J. David Smith, Arlington, MA (US); Rajeev Dhiman, Glastonbury, CT (US); Adam T. Paxson, Cambridge, MA (US); Christopher J. Love, Atlantis, FL (US); Brian R. Solomon, Rockville, MD (US); Kripa K. Varanasi, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/476,708

(22) Filed: Mar. 31, 2017

(65) Prior Publication Data
US 2018/0050133 A1  Feb. 22, 2018

Related U.S. Application Data

(63) Continuation of application No. 13/902,614, filed on May 24, 2013, now abandoned.
(Continued)

(51) Int. Cl.
*A61L 31/14* (2006.01)
*A61L 27/28* (2006.01)
(Continued)

(52) U.S. Cl.
CPC ............ *A61L 31/14* (2013.01); *A61K 9/0087* (2013.01); *A61K 9/025* (2013.01); *A61K 9/2072* (2013.01);
(Continued)

(58) Field of Classification Search
CPC .......... A61L 31/14; A61L 27/28; A61L 27/34; A61L 27/50; A61L 28/0034;
(Continued)

(56) References Cited

U.S. PATENT DOCUMENTS 4,069,933 A  1/1978  Newing
4,125,152 A  11/1978  Kestner et al.
(Continued)

FOREIGN PATENT DOCUMENTS

CN  1721030 A  1/2006
CN  100344341 C  10/2007
(Continued)

OTHER PUBLICATIONS

International Search Report and Written Opinion for application PCT/US2011/061498 dated Jul. 31, 2012.
(Continued)

*Primary Examiner* — Trevor Love
(74) *Attorney, Agent, or Firm* — Wolf, Greenfield & Sacks, P.C.

(57) ABSTRACT

Described herein are medical devices and medical implements with high lubricity to flesh (or biological fluid) and/or inhibited nucleation on its surface. The device has a surface comprising an impregnating liquid and a plurality of micro-scale and/or nano-scale solid features spaced sufficiently close to stably contain the impregnating liquid therebetween. The impregnating liquid fills spaces between said solid features, the surface stably contains the impregnating liquid between the solid features, and the impregnating liquid is substantially held in place between the plurality of solid features regardless of orientation of the surface.

20 Claims, 8 Drawing Sheets

Related U.S. Application Data

(60) Provisional application No. 61/651,543, filed on May 24, 2012.

(51) Int. Cl.

| | | |
|---|---|---|
| *A61L 27/34* | (2006.01) | |
| *A61L 27/50* | (2006.01) | |
| *A61L 28/00* | (2006.01) | |
| *A61L 29/08* | (2006.01) | |
| *A61L 29/14* | (2006.01) | |
| *A61L 31/08* | (2006.01) | |
| *A61L 31/10* | (2006.01) | |
| *A61L 15/34* | (2006.01) | |
| *A61L 15/42* | (2006.01) | |
| *A61K 9/48* | (2006.01) | |
| *A61K 9/20* | (2006.01) | |
| *A61K 9/02* | (2006.01) | |
| *A61K 9/70* | (2006.01) | |
| *A61K 9/00* | (2006.01) | |

(52) U.S. Cl.
CPC ............ *A61K 9/4808* (2013.01); *A61K 9/703* (2013.01); *A61L 15/34* (2013.01); *A61L 15/42* (2013.01); *A61L 27/28* (2013.01); *A61L 27/34* (2013.01); *A61L 27/50* (2013.01); *A61L 28/0034* (2013.01); *A61L 28/0061* (2013.01); *A61L 28/0069* (2013.01); *A61L 29/08* (2013.01); *A61L 29/085* (2013.01); *A61L 29/14* (2013.01); *A61L 31/08* (2013.01); *A61L 31/10* (2013.01); *A61L 2400/10* (2013.01); *A61L 2400/12* (2013.01); *A61L 2400/18* (2013.01); *Y10T 428/24355* (2015.01); *Y10T 428/24372* (2015.01)

(58) Field of Classification Search
CPC .. A61L 28/0061; A61L 28/0069; A61L 29/08; A61L 29/085; A61L 29/14; A61L 31/08; A61L 31/10; A61L 15/34; A61L 15/42; A61K 9/4808; A61K 9/2072; A61K 9/025; A61K 9/703; A61K 9/0087
See application file for complete search history.

(56) References Cited

U.S. PATENT DOCUMENTS

| | | | |
|---|---|---|---|
| 4,204,021 | A | 5/1980 | Becker |
| 4,316,745 | A | 2/1982 | Blount |
| 4,503,099 | A | 3/1985 | Chang et al. |
| 4,780,211 | A | 10/1988 | Lien |
| 5,083,606 | A | 1/1992 | Brown et al. |
| 5,133,516 | A | 7/1992 | Marentic et al. |
| 5,154,741 | A | 10/1992 | da Costa Filho |
| 5,624,713 | A | 4/1997 | Ramer |
| 5,816,280 | A | 10/1998 | Rojey et al. |
| 5,817,898 | A | 10/1998 | Delion et al. |
| 5,853,802 | A | 12/1998 | Boyer et al. |
| 5,900,516 | A | 5/1999 | Talley et al. |
| 5,936,040 | A | 8/1999 | Costello et al. |
| 5,955,165 | A | 9/1999 | Zamora et al. |
| 6,028,234 | A | 2/2000 | Heinemann et al. |
| 6,093,862 | A | 7/2000 | Sinquin et al. |
| 6,216,472 | B1 | 4/2001 | Cathenaut et al. |
| 6,247,603 | B1 | 6/2001 | Farrell et al. |
| 6,329,490 | B1 | 12/2001 | Yamashita et al. |
| 6,389,820 | B1 | 5/2002 | Rogers et al. |
| 6,649,266 | B1 | 11/2003 | Gross et al. |
| 7,041,363 | B2 | 5/2006 | Krohmer et al. |
| 7,323,221 | B2 | 1/2008 | Heppekausen et al. |
| 7,458,384 | B1 | 12/2008 | Seal et al. |
| 7,597,148 | B2 | 10/2009 | O'Malley et al. |
| 7,622,197 | B2 | 11/2009 | Balow et al. |
| 7,687,593 | B2 | 3/2010 | Yamahiro et al. |
| 7,722,951 | B2 | 5/2010 | Li et al. |
| 7,887,934 | B2 | 2/2011 | Gentleman et al. |
| 7,892,660 | B2 | 2/2011 | Gentleman et al. |
| 7,897,271 | B2 | 3/2011 | Gentleman et al. |
| 7,901,798 | B2 | 3/2011 | Gentleman et al. |
| 7,977,267 | B2 | 7/2011 | Gentleman et al. |
| 7,985,451 | B2 | 7/2011 | Luzinov et al. |
| 8,003,178 | B2 | 8/2011 | Kim et al. |
| 8,057,922 | B2 | 11/2011 | Gentleman et al. |
| 8,057,923 | B2 | 11/2011 | Gentleman et al. |
| 8,062,775 | B2 | 11/2011 | Gentleman et al. |
| 8,173,279 | B2 | 5/2012 | Gentleman et al. |
| 8,178,219 | B2 | 5/2012 | Gentleman et al. |
| 8,222,172 | B2 | 7/2012 | Gentleman et al. |
| 8,235,096 | B1 | 8/2012 | Mahefkey et al. |
| 8,236,432 | B2 | 8/2012 | Gentleman et al. |
| 8,252,259 | B2 | 8/2012 | Seal et al. |
| 8,377,390 | B1 | 2/2013 | Brueck et al. |
| 8,535,779 | B1 | 9/2013 | Smith et al. |
| 8,574,704 | B2 | 11/2013 | Smith et al. |
| 8,859,090 | B2 | 10/2014 | Angelescu et al. |
| 8,940,361 | B2 | 1/2015 | Smith et al. |
| 9,254,496 | B2 | 2/2016 | Dhiman et al. |
| 9,309,162 | B2 | 4/2016 | Azimi et al. |
| 9,371,173 | B2 | 6/2016 | Smith et al. |
| 9,381,528 | B2 | 7/2016 | Dhiman et al. |
| 9,625,075 | B2 | 4/2017 | Smith et al. |
| 10,882,085 | B2 | 1/2021 | Smith et al. |
| 2002/0146540 | A1 | 10/2002 | Johnston et al. |
| 2002/0164443 | A1 | 11/2002 | Oles et al. |
| 2003/0017303 | A1 | 1/2003 | Sindo et al. |
| 2003/0037914 | A1 | 2/2003 | Inbe et al. |
| 2003/0096083 | A1 | 5/2003 | Morgan et al. |
| 2003/0134035 | A1 | 7/2003 | Lamb et al. |
| 2003/0203117 | A1 | 10/2003 | Bartkowiak et al. |
| 2003/0226806 | A1 | 12/2003 | Young et al. |
| 2004/0003619 | A1 | 1/2004 | Lee et al. |
| 2004/0026832 | A1 | 2/2004 | Gier et al. |
| 2004/0037961 | A1 | 2/2004 | Dileman et al. |
| 2004/0219373 | A1 | 11/2004 | Deruelle et al. |
| 2004/0243249 | A1 | 12/2004 | Ishihara et al. |
| 2005/0003146 | A1 | 1/2005 | Spath |
| 2005/0009953 | A1 | 1/2005 | Shea |
| 2005/0016489 | A1 | 1/2005 | Endicott et al. |
| 2005/0061221 | A1 | 3/2005 | Paszkowski |
| 2005/0112326 | A1 | 5/2005 | Nun et al. |
| 2005/0136217 | A1 | 6/2005 | Barthlott et al. |
| 2005/0208272 | A1 | 9/2005 | Groll |
| 2006/0007515 | A1 | 1/2006 | Simonian et al. |
| 2006/0013735 | A1 | 1/2006 | Engelking et al. |
| 2006/0078724 | A1 | 4/2006 | Bhushan et al. |
| 2006/0147675 | A1 | 7/2006 | Nun et al. |
| 2006/0204738 | A1 | 9/2006 | Dubrow et al. |
| 2006/0240218 | A1 | 10/2006 | Parce |
| 2006/0246226 | A1 | 11/2006 | Dai et al. |
| 2007/0026193 | A1 | 2/2007 | Luzinov et al. |
| 2007/0031639 | A1 | 2/2007 | Hsu et al. |
| 2007/0135602 | A1 | 6/2007 | Yamahiro et al. |
| 2007/0207335 | A1 | 9/2007 | Karandikar et al. |
| 2007/0231542 | A1 | 10/2007 | Deng et al. |
| 2007/0282247 | A1 | 12/2007 | Desai et al. |
| 2007/0298216 | A1 | 12/2007 | Jing et al. |
| 2008/0026505 | A1 | 1/2008 | Chakrapani |
| 2008/0085070 | A1 | 4/2008 | Hirata et al. |
| 2008/0118763 | A1 | 5/2008 | Balow et al. |
| 2008/0145631 | A1 | 6/2008 | Bhate et al. |
| 2008/0213461 | A1 | 9/2008 | Gill et al. |
| 2008/0225378 | A1 | 9/2008 | Weikert et al. |
| 2009/0124520 | A1 | 5/2009 | Tohidi |
| 2009/0155609 | A1 | 6/2009 | Gentleman et al. |
| 2009/0185867 | A1 | 7/2009 | Masters et al. |
| 2009/0211735 | A1 | 8/2009 | Stenkamp et al. |
| 2009/0231273 | A1 | 9/2009 | Lashina et al. |
| 2009/0289213 | A1 | 11/2009 | Pipper |
| 2010/0004373 | A1 | 1/2010 | Zhu et al. |
| 2010/0028604 | A1 | 2/2010 | Bhushan et al. |
| 2010/0028615 | A1 | 2/2010 | Hwang et al. |
| 2010/0092621 | A1 | 4/2010 | Akutsu et al. |

(56) References Cited

U.S. PATENT DOCUMENTS

| | | |
|---|---|---|
| 2010/0098909 A1 | 4/2010 | Reyssat et al. |
| 2010/0112286 A1 | 5/2010 | Bahadur et al. |
| 2010/0135949 A1 | 6/2010 | Ou-Yang |
| 2010/0143620 A1 | 6/2010 | Ajdelsztajn et al. |
| 2010/0147441 A1 | 6/2010 | Nakagawa et al. |
| 2010/0151197 A1 | 6/2010 | Gentleman et al. |
| 2010/0180952 A1 | 7/2010 | Verhelst et al. |
| 2010/0200094 A1 | 8/2010 | Ermakov |
| 2010/0218517 A1 | 9/2010 | Luther |
| 2010/0285229 A1 | 11/2010 | Elbahri et al. |
| 2010/0285275 A1 | 11/2010 | Baca et al. |
| 2010/0307922 A1 | 12/2010 | Wu |
| 2010/0330146 A1 | 12/2010 | Chauhan et al. |
| 2010/0330340 A1 | 12/2010 | Rothstein et al. |
| 2011/0003143 A1 | 1/2011 | Sugimoto et al. |
| 2011/0042850 A1 | 2/2011 | Hong et al. |
| 2011/0077172 A1 | 3/2011 | Aizenberg et al. |
| 2011/0094883 A1 | 4/2011 | Ito et al. |
| 2011/0106504 A1 | 5/2011 | Noureldin |
| 2011/0201984 A1 | 8/2011 | Dubrow et al. |
| 2011/0226998 A1 | 9/2011 | Van De Weijer-Wagemans et al. |
| 2011/0240130 A1 | 10/2011 | Den Dulk et al. |
| 2011/0283778 A1 | 11/2011 | Angelescu et al. |
| 2011/0287217 A1 | 11/2011 | Mazumder et al. |
| 2012/0000848 A1 | 1/2012 | Lyons et al. |
| 2012/0000853 A1 | 1/2012 | Tuteja et al. |
| 2012/0036846 A1 | 2/2012 | Aizenberg et al. |
| 2012/0128963 A1 | 5/2012 | Mao et al. |
| 2012/0248020 A1 | 10/2012 | Granick et al. |
| 2013/0003258 A1 | 1/2013 | Xie et al. |
| 2013/0032316 A1 | 2/2013 | Dhiman et al. |
| 2013/0034695 A1 | 2/2013 | Smith et al. |
| 2013/0062285 A1 | 3/2013 | Hoek et al. |
| 2013/0122225 A1 | 5/2013 | Azimi et al. |
| 2013/0123389 A1 | 5/2013 | Zhu et al. |
| 2013/0146536 A1 | 6/2013 | Tarabara et al. |
| 2013/0220813 A1 | 8/2013 | Anand et al. |
| 2013/0227972 A1 | 9/2013 | Hatton et al. |
| 2013/0251769 A1 | 9/2013 | Smith et al. |
| 2013/0251942 A1 | 9/2013 | Azimi et al. |
| 2013/0251946 A1 | 9/2013 | Azimi et al. |
| 2013/0251952 A1 | 9/2013 | Smith et al. |
| 2013/0302405 A1 | 11/2013 | Takaha et al. |
| 2013/0333789 A1 | 12/2013 | Smith et al. |
| 2013/0335697 A1 | 12/2013 | Smith et al. |
| 2013/0337027 A1 | 12/2013 | Smith et al. |
| 2013/0340840 A1 | 12/2013 | Anand et al. |
| 2014/0141263 A1 | 5/2014 | Jones et al. |
| 2014/0147627 A1 | 5/2014 | Aizenberg et al. |
| 2014/0178611 A1 | 6/2014 | Smith et al. |
| 2014/0290699 A1 | 10/2014 | Bengaluru Subramanyam et al. |
| 2014/0291420 A1 | 10/2014 | Dhiman et al. |
| 2015/0111063 A1 | 4/2015 | Khan et al. |
| 2015/0125575 A1 | 5/2015 | Smith et al. |
| 2015/0179321 A1 | 6/2015 | Kahlil et al. |
| 2015/0306642 A1 | 10/2015 | Smith et al. |
| 2016/0150793 A1 | 6/2016 | Cordero et al. |
| 2016/0296985 A1 | 10/2016 | Dhiman et al. |
| 2017/0144828 A1 | 5/2017 | Smith et al. |
| 2017/0151575 A1 | 6/2017 | Dhiman et al. |
| 2018/0072895 A1 | 3/2018 | Smith et al. |
| 2018/0161836 A1 | 6/2018 | Anand et al. |
| 2018/0180364 A1 | 6/2018 | Dhiman et al. |
| 2019/0100353 A1 | 4/2019 | Subramanyam et al. |
| 2019/0224695 A1 | 7/2019 | Dhiman et al. |

FOREIGN PATENT DOCUMENTS

| | | |
|---|---|---|
| CN | 102002298 A | 4/2011 |
| CN | 101269960 B | 5/2011 |
| CN | 102790021 | 11/2012 |
| DE | 19818956 A1 | 11/1998 |
| EP | 0 230 112 A2 | 7/1987 |
| EP | 0 980 747 A2 | 2/2000 |
| EP | 1 892 458 A1 | 2/2008 |
| EP | 2163295 A1 | 3/2013 |
| JP | S60-75236 A | 4/1985 |
| JP | H01-170932 A | 7/1989 |
| JP | H05-240251 A | 9/1993 |
| JP | 2002-120861 | 4/2002 |
| JP | 2004-037764 A | 2/2004 |
| JP | 2006-143988 A | 6/2006 |
| JP | 2007-215620 A | 8/2007 |
| JP | 2007-278090 A | 10/2007 |
| JP | 2008-223003 A | 9/2008 |
| JP | 2008-240910 A | 10/2008 |
| JP | 2009-241943 A | 10/2009 |
| JP | 2010-167929 A | 8/2010 |
| JP | 2011-500150 A | 1/2011 |
| JP | 2011-126080 A | 6/2011 |
| JP | 2013-166811 A | 8/2013 |
| JP | 2013-168399 A | 8/2013 |
| KR | 10-2009-0020008 A | 2/2009 |
| TW | I233968 B | 6/2005 |
| WO | WO 93/17077 A1 | 9/1993 |
| WO | WO 99/36490 A1 | 7/1999 |
| WO | WO 01/38288 A1 | 5/2001 |
| WO | WO 02/62568 A2 | 8/2002 |
| WO | WO 03/13827 A1 | 2/2003 |
| WO | WO 03/71275 A1 | 8/2003 |
| WO | WO 2003/087604 A1 | 10/2003 |
| WO | WO 2006/017009 A2 | 2/2006 |
| WO | WO 2006/091235 A1 | 8/2006 |
| WO | WO 2006/132892 A2 | 12/2006 |
| WO | WO 2007/019362 A1 | 2/2007 |
| WO | WO 2008/111603 A1 | 9/2008 |
| WO | 2009/009185 A2 | 1/2009 |
| WO | WO 2010/028752 A1 | 3/2010 |
| WO | WO 2010/082710 A1 | 7/2010 |
| WO | WO 2010/096073 A1 | 8/2010 |
| WO | WO 2010/129807 A1 | 11/2010 |
| WO | WO 2011/087458 A1 | 7/2011 |
| WO | WO 2011/143371 A1 | 11/2011 |
| WO | WO 2012/024099 A1 | 2/2012 |
| WO | WO 2012/100099 A2 | 7/2012 |
| WO | WO 2012/100100 A2 | 7/2012 |
| WO | 2013/022467 A2 | 2/2013 |
| WO | 2013/130118 A1 | 9/2013 |
| WO | 2013/141888 A1 | 9/2013 |
| WO | 2013/141953 A2 | 9/2013 |
| WO | 2013/177579 A2 | 11/2013 |
| WO | WO 2014/123217 A1 | 8/2014 |

OTHER PUBLICATIONS

International Search Report and Written Opinion for application PCT/US2014/066227 dated Mar. 3, 2015.
International Preliminary Report on Patentability (Chapter II) for application PCT/US2014/066227 dated Feb. 2, 2016.
International Search Report and Written Opinion for application PCT/US2011/061898 dated Apr. 24, 2013.
International Search Report and Written Opinion for application PCT/US2012/030370 dated Oct. 15, 2012.
International Search Report and Written Opinion for application PCT/US2012/042327 dated May 16, 2013.
International Search Report and Written Opinion for application PCT/US2013/021558 dated Oct. 11, 2013.
International Search Report and Written Opinion for application PCT/US2013/042771 dated May 26, 2014.
International Search Report and Written Opinion for application PCT/US2012/042326 dated Dec. 3, 2012.
International Search Report and Written Opinion for application PCT/US2013/045731 dated Nov. 12, 2013.
International Search Report and Written Opinion for application PCT/US2014/019532 dated Nov. 25, 2014.
International Search Report and Written Opinion for application PCT/US2013/070827 dated Mar. 27, 2014.
International Preliminary Report on Patentability (Chapter II) for application PCT/US2013/070827 dated Feb. 10, 2015.
International Search Report and Written Opinion for application PCT/US2011/049187 dated Jan. 23, 2013.

(56) References Cited

OTHER PUBLICATIONS

International Search Report and Written Opinion for application PCT/US2012/065627 dated Mar. 8, 2013.
International Search Report and Written Opinion for application PCT/US2013/028439 dated Dec. 5, 2013.
[No Author Listed], Fluorinert Liquids for Electronics Manufacturing. 2003. 3M Corporation. 4 pages.
[No Author Listed], Furaipan curabu (frying pan club). Nov. 21, 2011. Last accessed on Nov. 3, 2016 from <https://www.furaipan.com/kaigi/11/1121.shtml>. 3 pages.
[No Author Listed], How much is left in that container? Consumer reports. Sep. 2009. Last accessed on May 21, 2015 at <http://www.consumerreports.org/cro/magazine-archive/september-2009/personal-finance/good-to-the-last-drop/overview/good-to-the-last-drop-ov.htm?view=print>. 2 pages.
[No Author Listed], Liquiglide gets it all out. Packaging News. Mar. 30, 2015. Last accessed on May 21, 2015 at <http://www.packagingnews.com.au/news/liquiglide-gets-it-all-out>. 4 pages.
[No Author Listed], LiquiGlide Lets Food Slide Out of Packaging with Ease. Food Processing. 2014. Last accessed on May 21, 2015 at <http://www.foodprocessing.com/vendors/products/2014/liquiglide-lets-food-slide-out-of-packaging-with-ease>. 6 pages.
[No Author Listed], Liquiglide's Coatings Ensure Evacuation of Viscous Formulations. Beauty Packaging. Aug. 4, 2014. Last accessed on May 21, 2015 at <http://www.beautypackaging.com/issues/2014-08/view_design-center/liquiglides-coatings-ensure-evacuation-of-viscous-formulations/>. 1 page.
[No Author Listed], Scientists Develop Super-Slippery Material. Slashdot. Original Nov. 14, 2011 post with public comments. Last accessed on Nov. 3, 2016 from <https://science.slashdot.org/story/11/11/14/0437204/scientists-develop-super-slippery-material>. 11 pages.
[No Author Listed], Super Slippery surface processing Harvard University Development. Science SRAD. Original Nov. 17, 2011 post with public comments. Last accessed on Nov. 3, 2016 from <http://science.srad.jp/story/11/11/17/0037255/>. 8 pages.
[No Author Listed], What is fluid? Heishin Ltd. 2014. Last accessed on Nov. 3, 2016 from <http://www.mohno-pump.co.jp/learning/manabiya/c2b.html>. 2 pages.
Allain et al., A New Method for Contact-Angle Measurements of Sessile Drops. Journal of Calloid and Interface Science. Sep. 1985;107(1):5-13.
Anand et al., Enhanced condensation on lubricant-impregnated nanotextured surfaces. ACS Nano. Nov. 27, 2012;6(11):10122-9. doi: 10.1021/nn303867y.
Antonini et al., Water drops dancing on ice: how sublimation leads to drop rebound. Phys Rev Lett. Jul. 5, 2013;111(1):014501-1-5.
Arkles, Hydrophobicity, Hydrophilicity and Silanes. Paint and Coatings Industry. Oct. 1, 2006;114-35.
Ashkin et al., Optical levitation by radiation pressure. Applied Physics Letters. 1971;19(8):283-5.
Ashkin et al., Optical levitation of liquid drop by radiation pressure. Science. 1975;187(4181):1073-5.
Avedisian et al., Leidenfrost boiling of methanol droplets on hot porous/ceramic surfaces. International Journal of Heat and Mass Transfer. 1987;30(2):379-93.
Azimi et al., Hydrophobicity of rare-earth oxide ceramics. Nat Mater. Apr. 2013;12(4):315-20. doi: 10.1038/nmat3545. Epub Jan. 20, 2013.
Baier et al., Propulsion Mechanisms for Leidenfrost Solids on Ratchets. Physical Review E-Statisitical, Nonlinear, and Soft Matter Physics. 2013;87(2).
Baier et al., Propulsion Mechanisms for Leidenfrost Solids on Ratchet Surfaces. arXiv preprint arXiv:1208.5721 (2012). 5 pages.
Bargir et al., The use of contact angle measurements to estimate the adhesion propensity of calcium carbonate to solid substrates in water. Applied Surface Science. 2009;255:4873-9.
Barnes, The Potential for Monolayers to Reduce the Evaporation of Water from Large Water Storages. Agricultural Water Management. 2008;95(4):339-53.

Bauer et al., The insect-trapping rim of Nepenthes pitchers: surface structure and function. Plant Signaling & Behavior. 2009;4(11):1019-23.
Beaugnon et al., Dynamics of magnetically levitated droplets. Physica B. 2001;294-295:715-20.
Betz et al., Do surfaces with mixed hydrophilic and hydrophobic areas enhance pool boiling? Applied Physics Letters. 2010;97:141909-1-3.
Biance et al., Leidenfrost drops. Physics of Fluids. 2003;15(6):1632-7.
Bico et al., Pearl drops. Europhysics Letters. 1999;47(2):220-6.
Bird et al., Reducing the contact time of a bouncing drop. Nature. Nov. 21, 2013;503(7476):385-8. doi: 10.1038/nature12740.
Blossey, Self-cleaning surfaces—Virtual realities. Nature Materials. 2003;2(5):301-6.
Bohn et al., Insect aquaplaning: Nepenthes pitcher plants capture prey with the peristome, a fully wettable water-lubricated anisotropic surface. Proc Natl Acad Sci U S A. Sep. 28, 2004;101(39):14138-43.
Burton et al., Geometry of the Vapor Layer Under a Leidenfrost Drop. Physical Review Letters. 2012;109(7):074301. 4 pages.
Cao et al., Anti-Icing Superhydrophobic Coatings. Langmuir Letter. 2009;25(21):12444-8.
Cassie et al., Wettability of porous surfaces. Transactions of the Faraday Society. 1944;40:546-51.
Celestini et al., Take Off of Small Leidenfrost Droplets. Physical Review Letters. 2012;109(3):034501-1-5.
Chandra et al., Leidenfrost evaporation of liquid nitrogen droplets. Transactions of the ASME: Journal of Heat Transfer. 1994;116(4):999-1006.
Chandra et al., Observations of droplet impingement on a ceramic porous surface. International Journal of Heat and Mass Transfer. 1992;35(10):2377-88.
Chaudhuri et al., Dynamic contact angles on PTFE surface by aqueous surfactant solution in the absence and presence of electrolytes. J Colloid Interface Sci. Sep. 15, 2009;337(2):555-62. doi: 10.1016/j.jcis.2009.05.033. Epub May 21, 2009.
Chen et al., A Wettability Switchable Surface by Microscale Surface Morphology Change. Journal of Micromechanics & Microengineering. Institute of Physics Publishing. 2007;17(3):489-95.
Cummings et al., Oscillations of magnetically levitated aspherical droplets. Journal of Fluid Mechanics. 1991;224:395-416.
Deng et al., Nonwetting of impinging droplets on textured surfaces. Applied Physics Letters. 2009;94(13):133109-1-3.
Dickerson, Incredible new invention has solved a universally annoying problem. Business Insider. Mar. 23, 2015. Accessed on May 21, 2015 at <http://www.businessinsider.com/liquiglide-nonstick-coating-on-bottles-2015-3>. 4 pages.
Eck et al., Growth and thermal properties of ultrathin cerium oxide layers on RH(111). Surface Science. 2002;520:173-85.
Elbahri et al., Anti-lotus effect for nanostructuring at the leidenfrost temperature. Advance Materials. 2007;19(9):1262-6.
Feng et al., Design and creation of superwetting/antiwetting surfaces. Advanced Materials. 2006;18(23):3063-78.
Fondecave et al., Polymers as Dewetting Agents. Macromolecules. 1998;31:9305-15.
Fujimoto et al., Deformation and rebounding processes of a water droplet impinging on a flat surface above Leidenfrost temperature. Journal of Fluids Engineering. Transactions of the ASME—Journal of Fluids Engineering. 1996;118(1):142-9.
Furmidge, Studies at Phase Interfaces. Journal of Colloid Science. 1962;17:309-24.
Gao et al., Artificial lotus leaf prepared using a 1945 patent and a commercial textile. Langmuir. 2006;22(14):5998-6000.
Goldshtik et al., A liquid drop on an air cushion as an analogue of Leidenfrost boiling. Journal of Fluid Mechanics. 1986;166:1-20.
Good, Contact angle, wetting and adhesion: a critical review. J. Adhesion Sci. Technol. 1992;6(12):1269-302.
Grace, Energy from Gas Hydrates: Assessing the Opportunities and Challenges for Canada. Council of Canadian Academies. Jul. 2008. 8 pages.

(56) References Cited

OTHER PUBLICATIONS

Gradeck et al., Heat transfer for Leidenfrost drops bouncing onto hot surface. Experimental Thermal and Fluid Science. 2013;47:14-25.
Hashmi et al., Leidenfrost levitation: beyond droplets. Sci Rep. 2012;2:797. doi: 10.1038/srep00797. 4 pages.
Hejazi et al., Wetting Transition in Two-, Three-, and Four-Phase Systems. Langmuir. 2012;28:2173-80.
Hirano, A study of Burning of Iron Fryingpan in Cooking. Journal of Home Economics of Japan. 1977;28(6):398-402.
Holden et al., The Use of Organic Coating to Promote Dropwise Condensation of Steam. Journal of Heat Transfer. 1987;109:768-74.
Iwasa et al., Electromaglev—Magnetic levitation of superconducting disc with a DC field generated by electromagnets: Part 1. Theoretical and experimental results on operating modes, lift-to-weight ratio, and suspension stiffness. Cryogenics. 1997;37(12):807-16.
Jung et al., Are Superhydrophobic Surfaces Best for Icephobicity? Langmuir. 2011;27(6):3059-66.
Kazi et al., Mineral Scale Formation and Mitigation on Metals and a Polymeric Heat Exchanger Surface. Applied Thermal Engineering. 2010;30:2236-42.
Kazi, Heat Exchangers—Basics Design Applications. Chapter 19—Fouling and Fouling Mitigation on Heat Exchanger Surfaces. InTech. Ed. Jovan Mitrovic. Mar. 2012:507-32.
Kim et al., Hierarchical or not? Effect of the length scale and hierarchy of the surface roughness on omniphobicity of lubricant-infused substrates. Nano Letters. 2013;13(4):1793-9.
Kim et al., Levitation Time Measurement of Water Drops on the Surface of Liquid Nitrogen. Journal of the Korean Physical Society. Jun. 2011;58(6):1628-32.
Kim, Floating Phenomenon of a Water Drop on the Surface of Liquid Nitrogen. Journal of the Korean Physical Society. Oct. 2006;49(4):L1335-8.
King, MIT Bottle Coating Offers Promising Solution to Product Waste. Sustainable Brands. Jul. 9, 2012. Accessed on May 21, 2015 at <http://www.sustainablebrands.com/new_and_views/articles/mit-bottle-coating-offers-promising-solution-product-waste>. 2 pages.
Kulinich et al., Ice Adhesion on Super-Hydrophobic Surfaces. Applied Surface Science. 2009;225:8153-7.
Lafuma et al., Slippery Pre-Suffused Surfaces. EPL. 2011;96:56001-1-4.
Lagubeau et al., Leidenfrost on a ratchet. Nature Physics. 2011;7(5):395-8.
Lee et al., Dynamic Wetting and Spreading Characteristics of a Liquid Droplet Impinging on Hydrophobic Textured Surfaces. Langmuir. 2011;27:6565-73.
Leidenfrost, On the fixation of water in diverse fire. International Journal of Heat and Mass Transfer. 1966;9(11):1153-66.
Li et al., Dynamic Behavior of the Water Droplet Impact on a Textured Hydrophobic/Superhydrophobic Surface: The Effect of the Remaining Liquid Film Arising on the Pillars' Tops on the Contact Time. Langmuir. 2010;26(7):4831-8.
Linke et al., Self-propelled leidenfrost droplets. Physical Review Letters. 2006;96(15):154502-1-4.
Liu et al., Extreme wettability and tunable adhesion: biomimicking beyond nature? Soft Matter. 2012;8:2070-86.
Liu et al., Metallic Surfaces with Special Wettability. Nanoscale. 2011;3:825-38.
Marcus, Ions in Water and Biphysical Implications. 4.2: Surface Between Water and Another Liquid. 2012. p. 147. Table 4.1.
Marin et al., Capillary droplets on Leidenfrost micro-ratchets. arXiv preprint. arXiv:1210.4978. 2012. 9 pages.
Masubuchi, Interesting Rheology. Gijutsuhyoronsha. Jul. 25, 2010. pp. 104-106.
Matolin et al., Growth of ultra-thin cerium oxide layers on Cu(111). Surface Science. 2007;254:153-5.
Meuler et al., Exploiting Topographical Texture to Impact Icephobicity. ACS Nano. 2010;4(12):7048-52.
Mills, Pillow lavas and the Leidenfrost effect. Journal of the Geological Society. 1984;141(1):183-6.
Mishchenko et al., Design of ice-free nanostructured surfaces based on repulsion of impacting water droplets. ACS Nano. 2010;4(12):7699-707.
Mullins et al., Ordered cerium oxide thin films grown on Ru(0001) and Ni(111). Surface Science. 1999;429:186-98.
Nosonovsky et al., Multiscale effects and capillary interactions in functional biomimetic surfaces for energy conversion and green engineering. Phil. Trans. R. Soc. A. 2009;367:1511-39.
Onda et al., Super-water-repellent fractal surfaces. Langmuir. 1996;12(9):2125-7.
Ou et al., Laminar drag reduction in microchannels using ultrahydrophobic surfaces. Physics of Fluids. 2004;16(12):4635-43.
Park et al., A Numerical Study of the Effects of Superhydrophobic Surface on Skin-Friction Drag in Turbulent Channel Flow. Phys. Fluids. 2013;25:110815-1-11.
Piroird et al., Magnetic control of Leidenfrost drops. Physical Review E—Statistical, Nonlinear, and Soft Matter Physics. 2012:85(5):056311-1-4.
Pozzato et al., Superhydrophobic surfaces fabricated by nanoimprint lithography. Microelectronic Engineering. 2006;83:884-88.
Prat et al., On the effect of surface roughness on the vapor flow under Leidenfrost-Levitated droplets. Journal of Fluids Engineering. Transactions of the ASME—Journal of Fluids Engineering. 1995;117(3):519-25.
Quéré et al., Surfing the hot spot. Nature Materials. 2006;5(6):429-30.
Quéré, Leidenfrost dynamics. Annu. Rev. Fluid Mech. 2013:197-215.
Quéré, Non-sticking drops. Institute of Physics Publishing. Rep. Prog. Phys. 2005;68(11):2495-532.
Rausch et al., On the characteristics of Ion Implanted Metallic Surfaces Inducing Dropwise Condensation of Steam. Langmuir. 2010;26(8):5971-5.
Reyssat et al., Bouncing transitions on microtextured materials. Europhysics Letters. 2006;74(2):306-12.
Reyssat et al., Dynamical superhydrophobicity. Faraday Discussions. 2010;146:19-33.
Richard et al., Contact time of a bouncing drop. Nature. Jun. 20, 2002;417(6891):811-2.
Roosen et al., Optical levitation by means of two horizontal laser beams: a theoretical and experimental study. Physics Letters. 1976;59A(1):6-8.
Rothstein, Slip on superhydrophobic surfaces. Annual Review of Fluid Mechanics. 2010;42(1):89-109.
Rykaczewski et al., Mechanism of frost formation on lubricant-impregnated surfaces. Langmuir. Apr. 30, 2013;29(17):5230-8. doi: 10.1021/la400801s.
Santos et al., Modified Stainless Steel Surfaces Targeted to Reduce Fouling. J. Food Engineering. 2004;64:63-79.
Schierbaum et al., Ordered ultra-thin cerium oxide overlayers on Pt(111) single crystal surfaces studied by LEED and XPS. Surface Science. 1998;399:29-38.
Seiwert et al., Coating of a Textured Solid. J. Fluid Mech. 2011;669:55-63.
Sekeroglu et al., Transport of a soft cargo on a nanoscale ratchet. Applied Physics Letters. 2011;99(6):063703-1-3.
Sloan, Jr., Fundamental Principles and Applications of Natural Gas Hydrates. Nature Publishing Group. 2003:353-9.
Smith et al., Droplet Mobility on Lubricant-Impregnated Surfaces. Soft Matter. 2013;9:1772-80.
Smith, Liquid-encapsulating surfaces: overcoming the limitations of superhydrophobic surfaces for robust non-wetting and anti-icing surfaces. Bulleting of the American Physical Society. 2011. Abstract Only.
Snoeijer et al., Maximum size of drops levitated by an air cushion. Physical Review E—Statistical, Nonlinear, and Soft Matter Physics. 2009;79(3). 13 pages.
Song et al., Superhydrophobic Surfaces Produced by Applying a Self-Assembled Monolyaer to Silicon Micro/Nano-Textured Surfaces. Nano Research. 2009;2:143-50.

(56) References Cited

OTHER PUBLICATIONS

Song et al., Vitrification and levitation of a liquid droplet on liquid nitrogen. PNAS Early Edition. 2010:1-5.
Sum et al., Clathrate Hydrates: From Laboratory Science to Engineering Practice. American Chemical Society Ind. Eng. Chem. Res. Jul. 22, 2009;48(16):7457-65.
Sutara et al., Epitaxial growth of continuous $CeO_2$(111) ultra-thin films on Cu(111). Thin Solid Films. 2008;516:6120-4.
Trinh et al., The dynamics of ultrasonically levitated drops in an electric field. Physics of Fluids. 1996;8(1)43-61.
Tropmann et al., Completely superhydrophobic PDMS surfaces for microfluidics. Langmuir. Jun. 5, 2012;28(22):8292-5. doi: 10.1021/la301283m. Epub May 21, 2012.
Tuteja et al., Designing superoleophobic surfaces. Science. 2007;318(5856):1618-22.
Tuteja et al., Robust omniphobic surfaces. Proc Natl Acad Sci U S A. Nov. 25, 2008;105(47):18200-5. doi: 10.1073/pnas.0804872105.
Vakarelski et al., Drag reduction by leidenfrost vapor layers. Physical Review Letters. 2011;106(21):214501-1-4.
Vakarelski et al., Stabilization of Leidenfrost vapour layer by textured superhydrophobic surfaces. Nature. 2012;489(7415):274-7.
Varanasi et al., Frost formation and ice adhesion on superhydrophobic surfaces. Applied Physics Letters. 2010;97(23):234102-1-3.
Varanasi et al., Spatial Control in the Heterogeneous Nucleation of Water. Applied Physics Letters. 2009;95:094101-01-03.
Weber et al., Aero-acoustic levitation: A method for containerless liquid-phase processing at high temperatures. Review of Scientific Instruments. 1994;65(2):456-65.
Weickgenannt et al., Inverse-Leidenfrost phenomenon on nanofiber mats on hot surfaces. Physical Review E—Statistical, Nonlinear, and Soft Matter Physics. 2011;84(3):036310-1-9.
Weilert et al., Magnetic levitation and noncoalescence of liquid helium. Physical Review Letters. 1996;77(23):4840-3.
Welter et al., Acoustically levitated droplets—A new tool for micro and trace analysis. Fresenius Journal of Analytical Chemistry. 1997;357(3):345-50.
Wenzel, Resistance of Solid Surfaces to Wetting by Water. Industrial & Engineering Chemistry. 1936;28(8):988-94.
Wong et al., Bioinspired Self-Repairing Slippery Surfaces with Pressure-Stable Omniphobicity. Nature. 2011;477(7365):443-7.
Wong et al., Bioinspired Self-Repairing Slippery Surfaces with Pressure-Stable Omniphobicity. Nature. 2011;477(7365):443-7. Supplementary Information Included.
Würger, Leidenfrost gas ratchets driven by thermal creep. Physical Review Letters. 2011;107(16). 4 pages.
Yarin et al., On the acoustic levitation of droplets. Journal of Fluid Mechanics. 1998;356:65-91.
Yasuda et al., Levitation of metallic melt by using the simultaneous imposition of the alternating and the static magnetic fields. Journal of Crystal Growth. 2004;260(3-4):475-85.
Yu et al., Containerless solidification of oxide material using an electrostatic levitation furnace in microgravity. Journal of Crystal Growth. 2001;231(4):568-76.
Zhao et al., Dropwise condensation of Steam on Ion Implanted Condenser Surfaces. Heat Recovery Systems & CHP. 1994;14(5):525-34.

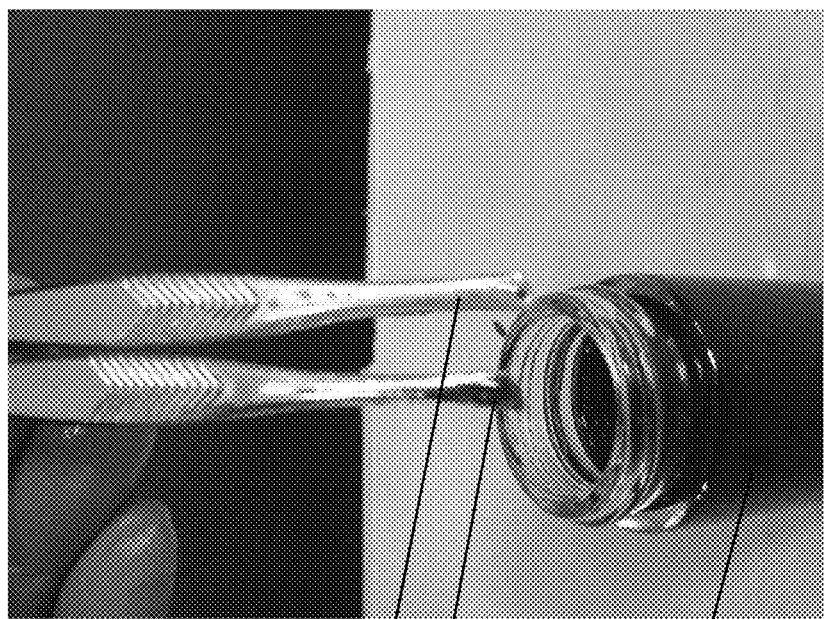
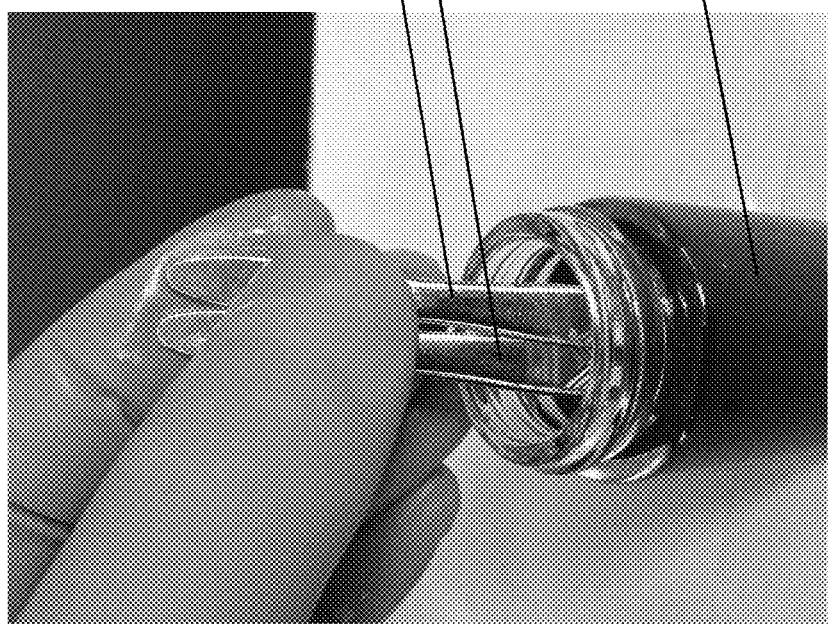
FIG. 2A
FIG. 2B

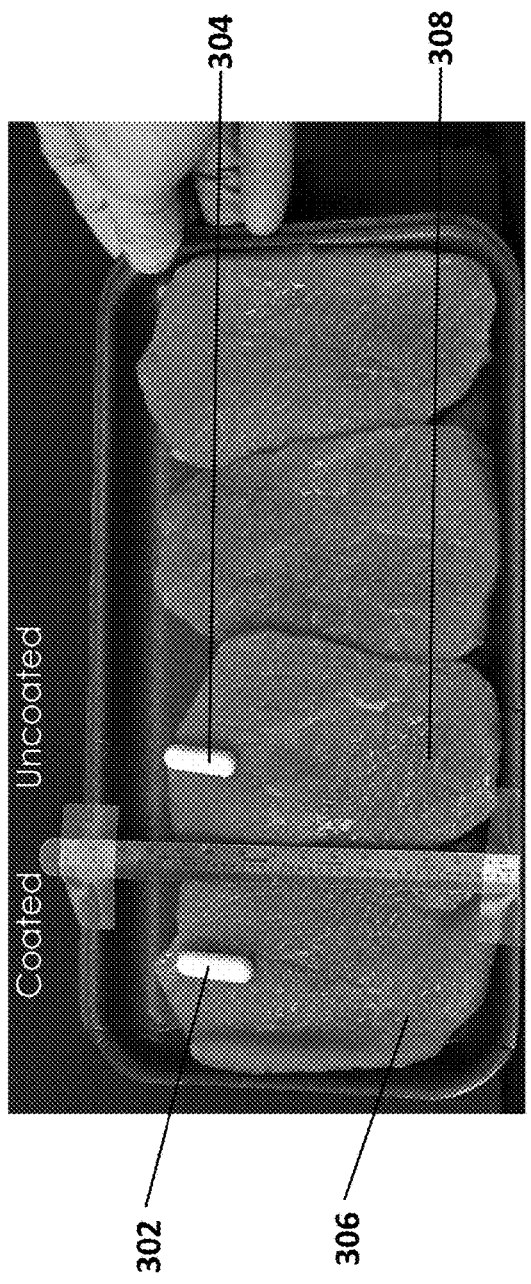 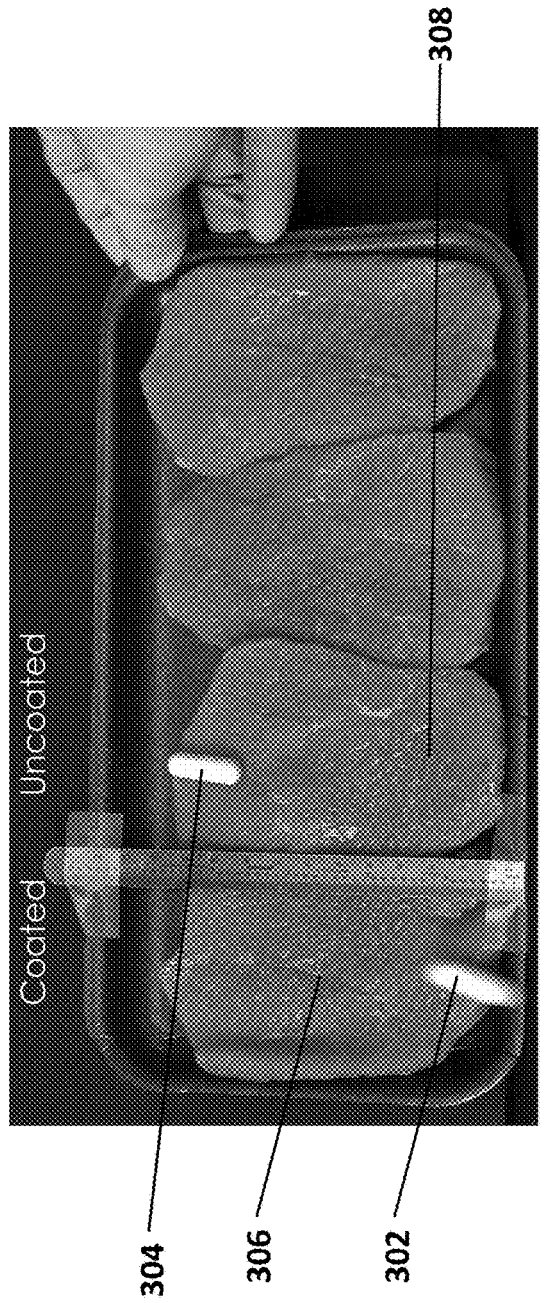
FIG. 3A
FIG. 3B

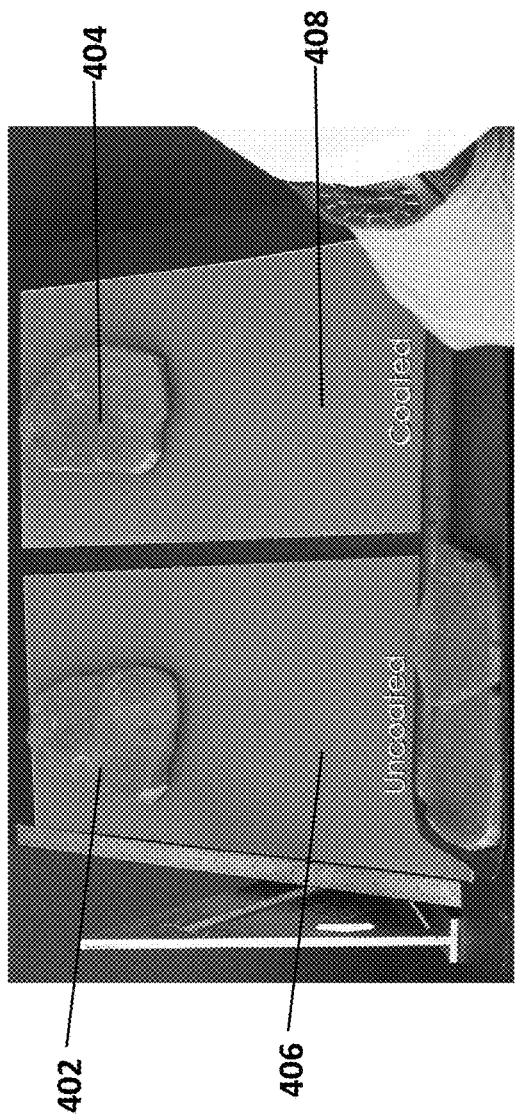
FIG. 4A
FIG. 4B

MEDICAL DEVICES AND IMPLEMENTS WITH LIQUID-IMPREGNATED SURFACES

RELATED APPLICATIONS

This application is a Continuation Application claiming priority to U.S. patent application Ser. No. 13/902,614, filed May 24, 2013, which claims priority to and the benefit of U.S. Provisional Patent Application No. 61/651,543, filed on May 24, 2012, each of which are hereby incorporated herein by reference in their entireties.

TECHNICAL FIELD

This invention relates generally to liquid-impregnated surfaces. More particularly, in certain embodiments, the invention relates to medical devices and implements with liquid-impregnated surfaces.

BACKGROUND

The advent of micro/nano-engineered surfaces in the last decade has opened up new techniques for enhancing a wide variety of physical phenomena in thermofluids sciences. For example, the use of micro/nano surface textures has provided nonwetting surfaces capable of achieving less viscous drag, reduced adhesion to ice and other materials, self-cleaning, and water repellency. These improvements result generally from diminished contact (i.e., less wetting) between the solid surfaces and adjacent liquids.

Liquid-impregnated surfaces are described in U.S. patent application Ser. No. 13/302,356, published as US 2013/0032316, entitled, "Liquid-Impregnated Surfaces, Methods of Making, and Devices Incorporating the Same," by Smith et al.; U.S. patent application Ser. No. 13/517,552, entitled, "Self-Lubricating Surfaces for Food Packaging and Food Processing Equipment," by Smith et al.; and U.S. Provisional Patent Application No. 61/827,444, filed May 24, 2013, entitled, "Apparatus and Methods Employing Liquid-Impregnated Surfaces," by Smith et al., the texts of which are incorporated herein by reference in their entireties.

There is a need for medical devices and implements with high lubricity to flesh (or biological fluid) and/or inhibited nucleation on the surface of the device/implement.

SUMMARY OF THE INVENTION

Described herein are medical devices and implements with liquid-impregnated surfaces for enhanced lubricity to flesh (or biological fluid) and/or inhibited nucleation on the surface of the device/implement.

In one aspect, the invention provides a medical device or medical implement with high lubricity to flesh (or biological fluid) and/or inhibited nucleation on its surface, the device or implement includes a surface comprising an impregnating liquid and a plurality of micro-scale and/or nano-scale solid features spaced sufficiently close to stably contain the impregnating liquid therebetween. In certain embodiments, the impregnating liquid fills spaces between said solid features and the surface stably contains the impregnating liquid between the solid features. In certain embodiments, the impregnating liquid is substantially held in place between the solid features regardless of orientation of the surface.

In certain embodiments, the solid features comprise particles having an average dimension in a range of 1 micron to 50 microns (e.g., 5 microns to 50 microns). The particles may be arranged with average spacing of about 1 micron to about 30 microns between adjacent particles or clusters of particles (e.g., 10 microns to 30 microns). The particles may be spray-deposited.

In certain embodiments, the impregnating liquid includes at least one member selected from the group consisting of ethyl oleate, an ester, a fatty acid, a fatty acid derivative, a vegetable oil (e.g., olive oil, light olive oil, corn oil, soybean oil, rapeseed oil, linseed oil, grapeseed oil, flaxseed oil, canola oil, peanut oil, safflower oil, sunflower oil), a terpene, phenyl isothiocyanate (phenyl mustard oil), bromobenzene, iodobenzene, o-bromotoluene, alpha-chloronaphthalene, alpha-bromonaphthalene, acetylene tetrabromide, 1-butyl-3-methylimidazolium bis(trifluoromethylsulfonyl) imide (BMIm), tribromohydrin (1,2,3-tribromopropane), ethylene dibromide, carbon disulfide, bromoform, methylene iodide (diiodomethane), stanolax, Squibb's liquid petrolatum, p-bromotoluene, monobromobenzene, perchloroethylene, carbon disulfide, phenyl mustard oil, monoiodobenzene, alpha-monochloro-naphthalene, acetylene tetrabromide, aniline, butyl alcohol, isoamyl alcohol, n-heptyl alcohol, cresol, oleic acid, linoleic acid, and amyl phthalate.

In certain embodiments, the solid features include one or more members selected from the group consisting of wax, carnauba wax, beeswax, candelilla wax, zein (from corn), dextrin, cellulose ether, hydroxyethyl cellulose, hydroxypropyl cellulose (HPC), hydroxyethyl methyl cellulose, hydroxypropyl methyl cellulose (HPMC), ethyl hydroxyethyl cellulose, insoluble fiber, purified wood cellulose, micro-crystalline cellulose, kaolinite (clay mineral), Japan wax, pulp (e.g., spongy part of plant stems), ferric oxide, iron oxide, sodium formate, sodium oleate, sodium palmitate, sodium sulfate, a metal, a polymer, a ceramic solid, a fluorinated solid, an intermetallic solid, and a composite solid PDMS, cyclic olefin polymer, polypropylene, PVC, PET, HDPE, polyimide, PMMA, glass, Perspex, Plexiglass, Polymacon.

The impregnating liquid may include an additive to prevent or reduce evaporation of the impregnating liquid. The medical device or medical implement may be a member selected from the group consisting of braces, dentures, a retainer, orthodonture, a bridge, an implant, a tooth/teeth mold, a prosthesis, an artificial organ, an artificial artery, a stent, a syringe, a lining (e.g., lining for artery walls to prevent plaque formation), an IV tube, an IV bag, a colostomy bag, a surgical instrument, a bandage, and a blood pump.

The medical device or medical implement may be a blood pump or part thereof. The surface may be configured to provide reduction of shear forces to prevent damage to cells and/or other biological structures in blood or other biological fluids being pumped thereby or therethrough. The medical device or medical implement may be a member selected from the group consisting of a pill, capsule (e.g., single-piece or two-piece), tablet, gel cap, and suppository.

The medical device or medical implement may be a member selected from the group consisting of a micropoipette, a small volume container of biological material, a human serum container, a pipette, a pipette tip, a microfluidic device, a dialysis machine, a tube, an endoscope, an intubation device, a syringe, a stent, a catheter, and a tracheotomy tube.

The medical device or medical implement may be a member selected from the group consisting of a glove, bandage, adhesive strip, drug release patch, and condom. The impregnating liquid may be an antiseptic and/or an antibacterial. The impregnating liquid may be curable and can be converted to a solid by curing (e.g., exposure to heat).

In some implementations, one or both of the following holds: (i) $0<\phi\leq0.25$, where $\phi$ is a representative fraction of the projected surface area of the liquid-impregnated surface corresponding to non-submerged solid at equilibrium; and (ii) $S_{ow(a)}<0$, where $S_{ow(a)}$ is spreading coefficient, defined as $\gamma_{wa}-\gamma_{wo}-\gamma_{oa}$, where $\gamma$ is the interfacial tension between the two phases designated by subscripts w, a, and o, where w is water, a is air, and o is the impregnating liquid. In some implementations, $0<\phi\leq0.25$. In some implementations, $0<\phi\leq0.10$. In some implementations, $0.01<\phi\leq0.25$. In some implementations, $0.01<\phi\leq0.10$. In some implementations, $S_{ow(a)}<0$.

In some implementations, one or both of the following holds: (i) $\theta_{os(w),receding}=0$; and (ii) $\theta_{os(a),receding}=0$ and $\theta_{os(w),receding}=0$, where $\theta_{os(w),receding}$ is receding contact angle of the impregnating liquid (e.g., oil, subscript 'o') on the surface (subscript 's') in the presence of water (subscript 'w'), and where $\theta_{os(a),receding}$ is receding contact angle of the impregnating liquid (e.g., oil, subscript 'o') on the surface (subscript 's') in the presence of air (subscript 'a').

BRIEF DESCRIPTION OF THE DRAWINGS

The objects and features of the invention can be better understood with reference to the drawing described below, and the claims.

FIGS. 2A and 2B demonstrate the effectiveness of liquid-impregnated surface coatings on tweezers to shed off blood;

FIGS. 3A and 3B demonstrate that liquid-impregnated surface pills slide more easily on animal tissue than uncoated pills;

FIGS. 4A and 4B demonstrate that animal flesh slides more easily on liquid-impregnated surfaces than on uncoated surfaces;

DETAILED DESCRIPTION

Figure 1:
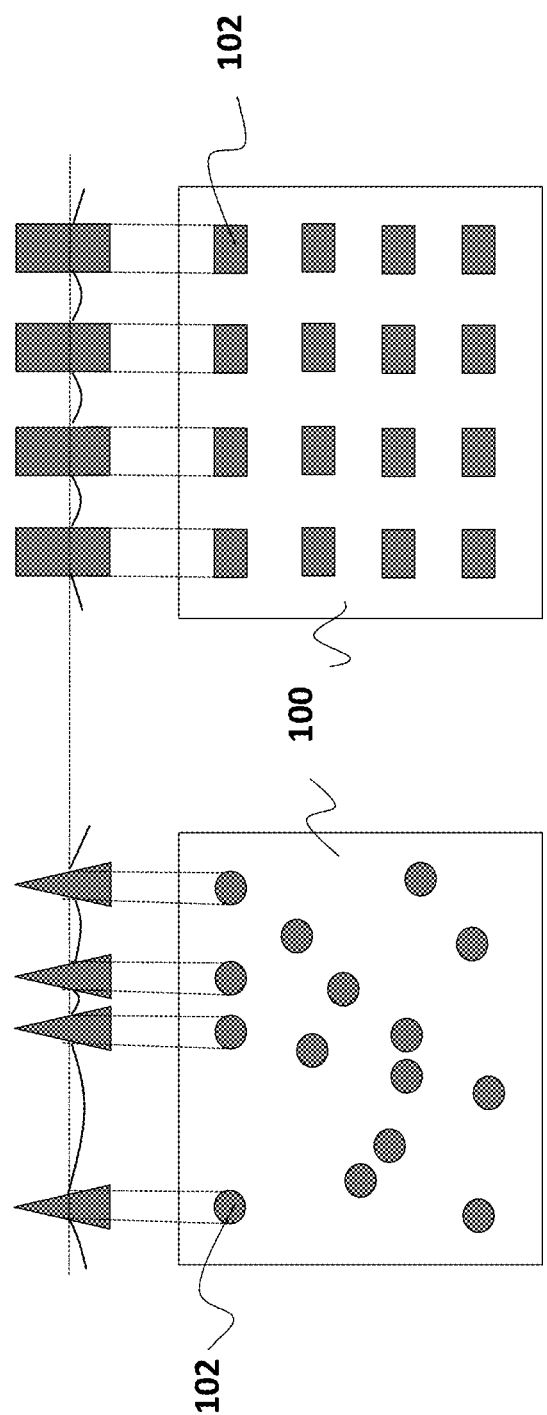
FIG. 1 illustrates a schematic cross-sectional and corresponding top view of a liquid-impregnated surface that are partially submerged.

It is contemplated that compositions, mixtures, systems, devices, methods, and processes of the claimed invention encompass variations and adaptations developed using information from the embodiments described herein. Adaptation and/or modification of the compositions, mixtures, systems, devices, methods, and processes described herein may be performed by those of ordinary skill in the relevant art.

Throughout the description, where articles, devices, apparatus and systems are described as having, including, or comprising specific components, or where processes and methods are described as having, including, or comprising specific steps, it is contemplated that, additionally, there are articles, devices, apparatus and systems of the present invention that consist essentially of, or consist of, the recited components, and that there are processes and methods according to the present invention that consist essentially of, or consist of, the recited processing steps.

Similarly, where articles, devices, mixtures, apparatus and compositions are described as having, including, or comprising specific compounds and/or materials, it is contemplated that, additionally, there are articles, devices, mixtures, apparatus and compositions of the present invention that consist essentially of, or consist of, the recited compounds and/or materials.

It should be understood that the order of steps or order for performing certain actions is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Described herein are surfaces comprising an impregnating liquid and a plurality of micro-scale and/or nano-scale solid features spaced sufficiently close to stably contain the impregnating liquid therebetween, wherein the impregnating liquid fills spaces between the solid features, wherein the interior surface stably contains the impregnating liquid between the solid features, and wherein the impregnating liquid is substantially held in place between the plurality of solid features.

In certain embodiments, the solid features may be part of the surface itself (e.g., the surface may be etched or otherwise textured to create the solid features), or the solid features may be applied to the surface. In certain embodiments, the solid features include an intrinsically hydrophobic, oleophobic, and/or metallophobic material or coating. For example, the solid features may be made of: hydrocarbons, such as alkanes, and fluoropolymers, such as teflon, trichloro(1H,1H,2H,2H-perfluorooctyl)silane (TCS), octadecyltrichlorosilane (OTS), heptadecafluoro-1,1,2,2-tetrahydrodecyltrichlorosilane, fluoroPOSS, and/or other fluoropolymers. Additional possible materials include: ceramics, polymeric materials, fluorinated materials, intermetallic compounds, and composite materials. Polymeric materials may include, for example, polytetrafluoroethylene, fluoroacrylate, fluoroeurathane, fluorosilicone, fluorosilane, modified carbonate, chlorosilanes, silicone, polydimethylsiloxane (PDMS), and/or combinations thereof. Ceramics may include, for example, titanium carbide, titanium nitride, chromium nitride, boron nitride, chromium carbide, molybdenum carbide, titanium carbonitride, electroless nickel, zirconium nitride, fluorinated silicon dioxide, titanium dioxide, tantalum oxide, tantalum nitride, diamond-like carbon, fluorinated diamond-like carbon, and/or combinations thereof. Intermetallic compounds may include, for example, nickel aluminide, titanium aluminide, and/or combinations thereof.

The solid features of a liquid-impregnated surface may form physical textures or surface roughness. The textures may be random, including fractal, or patterned. In certain embodiments, the textures are micro-scale or nano-scale features. For example, the textures may have a length scale L (e.g., an average pore diameter, or an average protrusion height) that is less than about 100 microns, less than about 10 microns, less than about 1 micron, less than about 0.1 microns, or less than about 0.01 microns. In certain embodiments, the texture includes posts or other protrusions, such as spherical or hemispherical protrusions. Rounded protrusions may be preferable to avoid sharp solid edges and minimize pinning of liquid edges. The texture may be introduced to the surface using any conventional method, including mechanical and/or chemical methods.

In certain embodiments, the solid features include particles. In certain embodiments, the particles have an average characteristic dimension in a range, for example, of about 5 microns to about 500 microns, or about 5 microns to about 200 microns, or about 10 microns to about 50 microns. In certain embodiments, the characteristic dimension is a diameter (e.g., for roughly spherical particles), a length (e.g., for roughly rod-shaped particles), a thickness, a depth, or a height. In certain embodiments, the particles include insoluble fibers, purified wood cellulose, micro-crystalline cellulose, oat bran fiber, kaolinite (clay mineral), Japan wax (obtained from berries), pulp (spongy part of plant stems), ferric oxide, iron oxide, sodium formate, sodium oleate, sodium palmitate, sodium sulfate, wax, carnauba wax, beeswax, candelilla wax, zein (from corn), dextrin, cellulose ether, Hydroxyethyl cellulose, Hydroxypropyl cellulose (HPC), Hydroxyethyl methyl cellulose, Hydroxypropyl methyl cellulose (HPMC), and/or Ethyl hydroxyethyl cellulose. In certain embodiments, the particles include a wax. In certain embodiments, the particles are randomly spaced. In certain embodiments, the particles are arranged with average spacing of about 1 micron to about 500 microns, or from about 5 microns to about 200 microns, or from about 10 microns to about 30 microns between adjacent particles or clusters of particles. In certain embodiments, the particles are spray-deposited (e.g., deposited by aerosol or other spray mechanism).

In some embodiments, micro-scale features are used. In some embodiments, a micro-scale feature is a particle. Particles can be randomly or uniformly dispersed on a surface. Characteristic spacing between particles can be about 200 μm, about 100 μm, about 90 μm, about 80 μm, about 70 μm, about 60 μm, about 50 μm, about 40 μm, about 30 μm, about 20 μm, about 10 μm, about 5 μm or 1 μm. In some embodiments, characteristic spacing between particles is in a range of 100 μm to 1 μm, 50 μm to 20 μm, or 40 μm to 30 μm. In some embodiments, characteristic spacing between particles is in a range of 100 μm to 80 μm, 80 μm to 50 μm, 50 μm to 30 μm or 30 μm to 10 μm. In some embodiments, characteristic spacing between particles is in a range of any two values above.

Particles can have an average dimension of about 200 μm, about 100 μm, about 90 μm, about 80 μm, about 70 μm, about 60 μm, about 50 μm, about 40 μm, about 30 μm, about 20 μm, about 10 μm, about 5 μm or 1 μm. In some embodiments, an average dimension of particles is in a range of 100 μm to 1 μm, 50 μm to 10 μm, or 30 μm to 20 μm. In some embodiments, an average dimension of particles is in a range of 100 μm to 80 μm, 80 μm to 50 μm, 50 μm to 30 μm, or 30 μm to 10 μm. In some embodiments, an average dimension of particles is in a range of any two values above.

In some embodiments, particles are porous. Characteristic pore size (e.g., pore widths or lengths) of particles can be about 5000 nm, about 3000 nm, about 2000 nm, about 1000 nm, about 500 nm, about 400 nm, about 300 nm, about 200 nm, about 100 nm, about 80 nm, about 50, about 10 nm. In some embodiments, characteristic pore size is in a range of 200 nm to 2 μm or 100 nm to 1 μm. In some embodiments, characteristic pore size is in a range of any two values above.

The impregnating liquid of a liquid-impregnating surface may be oil-based or water-based (i.e., aqueous). The liquid may be chosen for a given application based on its properties. In certain embodiments, the impregnating liquid is an ionic liquid (e.g., BMI-IM). Other examples of possible impregnating liquids include hexadecane, vacuum pump oils (e.g., FOMBLIN® 06/6, KRYTOX® 1506) silicon oils (e.g., 10 cSt or 1000 cSt), fluorocarbons (e.g., perfluorotripentylamine, FC-70), shear-thinning fluids, shear-thickening fluids, liquid polymers, dissolved polymers, viscoelastic fluids, and/or liquid fluoroPOSS. In one embodiment, the impregnating liquid is made shear thickening with the introduction of nano particles. A shear-thickening impregnating liquid may be desirable for preventing impalement and resisting impact from impinging liquids, for example. To minimize evaporation of the impregnating liquid from the surface, it may be desirable to use an impregnating liquid that has a low vapor pressure (e.g., less than 0.1 mmHg, less than 0.001 mmHg, less than 0.00001 mmHg, or less than 0.000001 mmHg). In certain embodiments, the impregnating liquid has a freezing point of less than −20° C., less than −40° C., or about −60° C. In certain embodiments, the surface tension of the impregnating liquid is about 15 mN/m, about 20 mN/m, or about 40 mN/m. In certain embodiments, the viscosity of the impregnating liquid is from about 10 cSt to about 1000 cSt.

The impregnating liquid may be introduced to the surface using a conventional technique for applying a liquid to a solid. In certain embodiments, a coating process, such as a dip coating, blade coating, or roller coating, is used to apply the impregnating liquid. Alternatively, the impregnating liquid may be introduced and/or replenished by liquid materials flowing past the surface. In preferred embodiments, after the impregnating liquid has been applied, capillary forces hold the liquid in place.

In certain embodiments, a texture may be applied to a substrate to form a surface with solid features. Applying the texture may include: exposing the substrate to a solvent (e.g., solvent-induced crystallization), extruding or blow-molding a mixture of materials, roughening the substrate with mechanical action (e.g., tumbling with an abrasive), spray-coating, polymer spinning, depositing particles from solution (e.g., layer-by-layer deposition and/or evaporating away liquid from a liquid and particle suspension), extruding or blow-molding a foam or foam-forming material (e.g., a polyurethane foam), depositing a polymer from a solution, extruding or blow-molding a material that expands upon cooling to leave a wrinkled or textured surface, applying a layer of material onto a surface that is under tension or compression, performing non-solvent induced phase separation of a polymer to obtain a porous structure, performing micro-contact printing, performing laser rastering, performing nucleation of the solid texture out of vapor (e.g., desublimation), performing anodization, milling, machining, knurling, e-beam milling, performing thermal or chemical oxidation, and/or performing chemical vapor deposition. In certain embodiments, applying the texture to the substrate includes spraying a mixture of edible particles onto the substrate. In certain embodiments, impregnating the matrix of features with the liquid includes: spraying the encapsulating liquid onto the matrix of features, brushing the liquid onto the matrix of features, submerging the matrix of features in the liquid, spinning the matrix of features, condensing the liquid onto the matrix of features, depositing a solution comprising the liquid and one or more volatile liquids, and/or spreading the liquid over the surface with a second immiscible liquid. In certain embodiments, the liquid is mixed with a solvent and then sprayed, because the solvent will reduce the liquid viscosity, allowing it to spray more easily and more uniformly. Then, the solvent will dry out of the coating. In certain embodiments, the method further includes chemically modifying the substrate prior to applying the texture to the substrate and/or chemically modifying the solid features of the texture. For example, the method may include chemically modifying with a material having contact angle with water of greater than 70 degrees (e.g., hydrophobic material). The modification may be conducted, for example, after the texture is applied, or may be applied to particles prior to their application to the substrate. In certain embodiments, impregnating the matrix of features includes removing excess liquid from the matrix of features. In certain embodiments, removing the excess liquid includes: using a second immiscible liquid to carry away the excess liquid, using mechanical action to remove the excess liquid, absorbing the excess liquid using a porous material, and/or draining the excess liquid off of the matrix of features using gravity or centrifugal forces.

Liquid-impregnated surfaces are useful for reducing viscous drag between a solid surface and a flowing liquid. In general, the viscous drag or shear stress exerted by a liquid flowing over a solid surface is proportional to the viscosity of the liquid and the shear rate adjacent to the surface. A traditional assumption is that liquid molecules in contact with the solid surface stick to the surface, in a so-called "no-slip" boundary condition. While some slippage may occur between the liquid and the surface, the no-slip boundary condition is a useful assumption for most applications. In certain embodiments, liquid-impregnated surfaces are desirable as they induce a large amount of slip at the solid surface. Drag reductions of as much as 40% may be achieved due to this slippage.

In certain embodiments, impregnating a liquid within the textures of a liquid-impregnated surface prevents or reduces nucleation in these regions. The reduction in nucleation is enhanced where liquid covers the tops of the solid features of the liquid-impregnated surface. Furthermore, in certain embodiments, liquid-impregnated surfaces have low roll-off angles (i.e., the angle or slope of a surface at which a droplet in contact with the surface will begin to roll or slide off the surface). The low roll-off angles associated with liquid-impregnated surfaces allow droplets in contact with the surface to easily roll off the surface before the liquid can accumulate on the surface. In certain embodiments, liquid-impregnated surfaces are used to provide hydrate-phobicity, thereby preventing or minimizing the formation of hydrates. In certain embodiments, liquid-impregnated surfaces are used to provide salt-phobicity, thereby preventing or minimizing the formation of salts or mineral scale.

In certain embodiments, liquid-impregnated surfaces are used to reduce viscous drag between a solid surface and a flowing liquid. In certain embodiments, a liquid-impregnated surface is used to provide lubrication between the liquid-impregnated surface and a substance in contact with the surface (or the surface itself, where one liquid-impregnated surface rubs against another liquid-impregnated surface, or parts of the liquid-impregnated surface rub against each other). For example, liquid-impregnated surfaces may provide significant slip/lubrication advantages when in contact with a substance that is a non-Newtonian material, a Bingham plastic, a thixotropic fluid, and/or a shear-thickening substance.

Liquid-impregnated surfaces may also provide anti-fouling and/or self-cleaning. Liquid-impregnated surfaces may also be used to promote the condensation of moisture.

As used herein, emerged area fraction $\phi$ is defined as a representative fraction of the projected surface area of (a representative fraction of) the liquid-impregnated surface corresponding to non-submerged solid at equilibrium (or pseudo-equilibrium). The term "equilibrium" as used herein refers to the condition in which the average thickness of the impregnating film does not substantially change over time due to drainage by gravity when the substrate is held away from horizontal, and where evaporation is negligible (e.g., if the liquid impregnated liquid were to be placed in an environment saturated with the vapor of that impregnated liquid). Similarly, the term "pseudo-equilibrium" as used herein refers to the same condition except that evaporation may occur.

In general, a "representative fraction" of a surface refers to a portion of the surface with a sufficient number of solid features thereupon such that the portion is reasonably representative of the whole surface. In certain embodiments, a "representative fraction" is at least a tenth of the whole surface.

In certain embodiments, $\phi$ is zero (there is a layer of liquid over the top of the solid features which may be, for example, at least 1 nm, at least 5 nm, at least 10 nm, or at least 100 nm in thickness). In certain embodiments of the present invention, $\phi$ is less than 0.30, 0.25, 0.20, 0.15, 0.10, 0.05, 0.01, or 0.005. In certain embodiments, $\phi$ is greater than 0.001, 0.005, 0.01, 0.05, 0.10, 0.15, or 0.20. In certain embodiments, $\phi$ is in a range of about 0 and about 0.25. In certain embodiments, $\phi$ is in a range of about 0 and about 0.01. In certain embodiments, $\phi$ is in a range of about 0.001 and about 0.25. In certain embodiments, $\phi$ is in a range of about 0.001 and about 0.10.

In some embodiments, the liquid-impregnated surface is configured such that cloaking by the impregnating liquid can be either eliminated or induced, according to different embodiments described herein.

As used herein, the spreading coefficient, $S_{ow(a)}$ is defined as $\gamma_{wa}-\gamma_{wo}-\gamma_{oa}$, where $\gamma$ is the interfacial tension between the two phases designated by subscripts w, a, and o, where w is water, a is air, and o is the impregnating liquid. Interfacial tension can be measured using a pendant drop method as described in Stauffer, C. E., "The measurement of surface tension by the pendant drop technique," *J. Phys. Chem.* 1965, 69, 1933-1938, the text of which is incorporated by reference herein. Exemplary surfaces and its interfacial tension measurements (at approximately 25° C.) are shown in Appendix D, in particular, Table S2.

Without wishing to be bound to any particular theory, impregnating liquids that have $S_{ow(a)}$ less than 0 will not cloak, resulting in no loss of impregnating liquids, whereas impregnating liquids that have $S_{ow(a)}$ greater than 0 will cloak matter (condensed water droplets, bacterial colonies, solid surface) and this may be exploited to prevent corrosion, fouling, etc. In certain embodiments, cloaking is used for preventing vapor-liquid transformation (e.g, water vapor, metallic vapor, etc.). In certain embodiments, cloaking is used for inhibiting liquid-solid formation (e.g., ice, metal, etc.). In certain embodiments, cloaking is used to make reservoirs for carrying the materials, such that independent cloaked materials can be controlled and directed by external means (like electric or magnetic fields).

In certain embodiments, lubricant cloaking is desirable and is used a means for preventing environmental contamination, like a time capsule preserving the contents of the cloaked material. Cloaking can result in encasing of the material thereby cutting its access from the environment. This can be used for transporting materials (such as bioassays) across a length in a way that the material is not contaminated by the environment.

In certain embodiments, the amount of cloaking can be controlled by various lubricant properties such as viscosity, surface tension. Additionally or alternatively, we can control the de-wetting of the cloaked material to release the material. Thus, it is contemplated that a system in which a liquid is dispensed in the lubricating medium at one end, and upon reaching the other end is exposed to environment that causes the lubricant to uncloak.

In some embodiments, an impregnating liquid can be selected to have a $S_{ow(a)}$ less than 0. Exemplary impregnating liquids include, but are not limited to, tetrachloroethylene (perchloroethylene), phenyl isothiocyanate (phenyl mustard oil), bromobenzene, iodobenzene, o-bromotoluene, alpha-chloronaphthalene, alpha-bromonaphthalene, acetylene tetrabromide, 1-butyl-3-methylimidazolium bis(trifluoromethylsulfonyl) imide (BMIm), tribromohydrin (1,2,3-tribromopropane), tetradecane, cyclohexane, ethylene dibromide, carbon disulfide, bromoform, methylene iodide (diiodomethane), stanolax, Squibb's liquid petrolatum, p-bromotoluene, monobromobenzene, perchloroethylene, carbon disulfide, phenyl mustard oil, monoiodobenzene, alpha-monochloro-naphthalene, acetylene tetrabromide, aniline, butyl alcohol, isoamyl alcohol, n-heptyl alcohol, cresol, oleic acid, linoleic acid, amyl phthalate and any combination thereof.

Referring to FIG. 1, a schematic cross-sectional view and the corresponding top view of a liquid-impregnated surface that is partially submerged is shown. The upper left drawing of FIG. 1 shows a cross-sectional view of a row of cone-shaped solid features. The projected surface area of the non-submerged solid 102 is illustrated as shaded areas of the overhead view, while the remaining non-shaded area represents the projected surface area of the submerged liquid-impregnated surface 100. In addition to the projection surface area of this row of solid features, other solid features placed in a semi-random pattern are shown in shade in the overhead view. Similarly, the cross-section view of a row of evenly spaced posts is shown on the right of FIG. 1. Additional rows of well-patterned posts are shown in shade in the overhead view. As demonstrated, in some embodiments of the present invention, a liquid-impregnated surface includes randomly and/or non-randomly patterned solid features.

In certain embodiments, a medical device or medical implement exhibits the nucleation show in FIG. 1 on its surface. The device's surface comprises an array of microscale or nano-scale solid features spaced sufficiently close to contain an impregnating liquid in between them. The impregnating liquid fills the spaces between the solid features, and the surface stably holds the impregnating liquid in place in between the solid features regardless of the orientation of the surface. In some implementations, the particles have an average dimension of 5 microns to 50 microns. In some implementations, the particles are arranged with average spacing of about 10 microns to about 30 microns between adjacent particles or clusters of particles.

In certain embodiments, the particles are coated onto the medical device or medical implement's surface by spray coating the surface with an impregnating liquid solution. The spray coating may apply a uniform coat of impregnating liquid to the surface of the medical device or medical implement. In certain implementations, the impregnating liquid may be spray coated onto the surface of the medical device in multiple stages. In certain implementations where the impregnating solution is composed of several different solutions, the various constituent solutions of the impregnating liquid may be spray coated onto the target surface in different stages.

The applications of liquid-impregnated surfaces for inhibiting nucleation may include, for example, preventing of nucleation of plaque on teeth, dentures, braces, or retainers. The applications of liquid-impregnated surfaces my also include, for example, preventing fibrosis on artificial implants. Furthermore, applications may also include preventing thrombosis on surfaces in contact with blood, or surfaces of tubes or artificial arteries or stents, which clog from build up of cholesterol or a solid-like materials. These surfaces would benefit from a more lubricated interface.

In some embodiments, the liquid-impregnated surface is created by applying a uniform layer of the impregnating liquid to a surface. In certain implementations, this surface may be human or animal tissue. A uniform layer of impregnating liquid may be sprayed onto a surface to create a uniform liquid-impregnated surface coating.

In some embodiments, the liquid-impregnated surface coating may be applied to the internal surface of a syringe for emptying out the contents of the syringe. For example, the internal surface of the syringe cylinder's barrel may be coated with the impregnating liquid. This will reduce the attractive forces between contents of the syringe and internal surface of the syringe cylinder's barrel to expel the maximum amount of the syringe's contents with less applied plunger force.

In some embodiments, the liquid-impregnated surface coating may be applied to an artificial or natural lining for artery walls to prevent plaque formation. The lining may be coated with the impregnating liquid in such a manner that does not allow plaque to stick to the lining of the artery walls easily. The impregnating liquid may be applied to the lining of the artery walls by pumping the artery walls with the impregnating liquid solution or by any surgical procedure.

In some embodiments, the liquid-impregnated surface coating may be applied to IV drips, the lining of IV tubes and the interior surfaces of IV bags. Such a coating would allow the content of an IV bag and/or tube to easily slide along the IV bag and tube with minimal waste of the content. By increasing the slipperiness of the IV lining, the liquid-impregnated surface coating reduces the attractive forces between the IV tubes and bags and their contents. This allows the content to be easily dispensed. For example, medical practitioners are frequently unable to convey an adequate flow rate of drugs to the patient because they cannot afford to put in a larger-gauge IV. Creation of a liquid-impregnated surface in the IV tube provides medical practitioners with the ability to convey an adequate flow rate of drugs to a patient without using a larger-gauge IV.

In some embodiments, the liquid-impregnated surface coating may be applied to colostomy bags. This allows for smooth reception of fecal discharge after colostomy more easily and reduces discomfort to the patient.

In some embodiments, the liquid-impregnated surface coating may be applied to teeth to prevent buildup of plaque. By applying such a coating, food particles and other plaque will be less likely to stick to teeth, thereby increasing dental health of the subject.

In some embodiments, the liquid-impregnated surface coating may be applied to metal or metallic surgical instruments, as shown by the experiment documented in FIGS. 2A and 2B as discussed below. Applying such a coating to surgical instrument allows bodily fluids such as blood to be repelled off the coated surgical instruments and allows the instrument to remain clean.

In some embodiments, the liquid-impregnated surface coating may be applied to bandages in order to allow the bandages to be easily removed from the skin without causing discomfort to the patient. For instance, bandages with such a liquid-impregnated surface coating do not become glued to the wound or skin very tightly over time and pressure and can be easily removed.

In some embodiments, the liquid-impregnated surface coating may be applied to blood pumps. Shear forces encountered in pumping blood and other biological fluids often damage or destroy cells by mechanically ripping them apart. The liquid-impregnated surface coating significantly reduced the shear forces at the surfaces of the pump to prevent damage of cells and other biological structures.

In some embodiments, the liquid-impregnated surface coating may be applied to lab supplies and pharmaceuticals in order for them to remain clean and prevent foreign substances from sticking to them.

In some embodiments, the liquid-impregnated surface coating may be applied to pills and capsules for ease of swallowing, as shown by the experiment documented in FIGS. 3A and 3B as discussed below. Applying such a coating to pills allows the coated pills to easily slide along the tongue and esophagus tissue by reducing the frictional force between the pill and human tissue.

In some embodiments, the liquid-impregnated surface coating may be applied to micropipettes, pipettes, pipette tips, small volume containers of biological fluids and samples. For small-volume containers and micropipettes, the proportion of the contents that remains stuck to the container represents a significant fraction of the total volume of the container. Furthermore, the contents are often expensive and labor-intensive to obtain. Applying the impregnated liquid coating to the interior surfaces of these containers and pipette tips allows the contents to be easily expelled from these containers with minimal waste. Similarly, the coating may also be applied to the contents of these containers, especially DNA and RNA strands which will aid in the easy expulsion of these compounds from the small volume containers.

In some embodiments, the liquid-impregnated surface coating may be applied to microfluidic devices. Often microfluidic channels become clogged with the contents being passed through these channels. By coating the microfluidic channels with liquid-impregnated surface coating, the contents of these microfluidic channels do not clog the channels and the microfluidic devices can remain operation for a longer period of time without any maintenance.

In some embodiments, the liquid-impregnated surface coating may be applied to dialysis tubes and other components of dialysis machines to facilitate easier for waste and excess water removal from the blood.

In some embodiments, the liquid-impregnated surface coating may be applied to any surgical tools that are inserted into the body such as endoscopes, stents, syringe needles, stents, catheters, tracheotomy tubes, and intubation devices. Such a coating, when applied to these surfaces, allows for a much easier insertion into the body without causing any undesired tears in body tissue. Such a coating allows for more comfortable insertion of intubation equipment. The encapsulated liquid in the coating may also contain mid antiseptic and an anesthetic that would allow for the local area of insertion to be anesthetized and clean while the surgical tool is being inserted. An experimented conducted using polypropylene sheets, used to simulate the surface of a surgical instrument, in contact with a steak, used to simulate human tissue, is shown in FIGS. 4A and 4B as discussed below.

In some embodiments, the liquid-impregnated surface coating may be applied to creams, prescription creams, ointments, Neosporin, triple antibiotic ointment, burn relieving cream, anti-itch cream, aloe-vera gel, sunscreen lotion, and other lotions. The coating may also be applied to containers of ointments, lotions, and creams. Such a coating would allow these chemicals to be easily dispensed and would prevent the last few drops of such cream, lotion of ointment to stick to the container walls.

In some embodiments, the liquid-impregnated surface coating may be applied to medical supplies, gloves, bandages for covering open wounds, bandages for skin conditions, medical implants, implant coatings in order to keep them clean from foreign particles.

In some embodiments, the liquid-impregnated surface coating may be applied to medical device surfaces, artificial heart, and artificial organs to prevent buildup of organic matter on these devices.

In some embodiments, the liquid-impregnated surface coating may be applied to prosthetics and self-lubricating joints in order to keep them free of dirt and organic matter buildup that could deteriorate effective operation.

In some embodiments, the liquid-impregnated surface coating may be applied to orthodontic tools such as a retainer, a tooth mold, dentures, dental braces, invisible braces. The surface coating can avoid plaque buildup on the surfaces of these orthodontic tools improving dental health and hygiene.

In some embodiments, the liquid-impregnated surface coating may be applied to bridges and wetted surfaces to avoid biofouling.

In some embodiments, the encapsulated liquid in the liquid-impregnated surface coating may be antiseptic and antibacterial in order to allow the surfaces to remain clean. This is particularly important in medical applications where the cleanliness of medical devices is paramount.

In some embodiments, the liquid-impregnated surface coating may be applied to adhesive strips. Liquid impregnated surfaces have strong capillary adhesive forces in the normal direction. The lateral forces depend on the impregnated liquid viscosity. An extremely high viscosity impregnated liquid can behave essentially as a solid, preventing sliding, and therefore the surface would behave similarly to tape. Low viscosity fluids slide easily, thus resulting in an surface that behave as an adhesive in the normal direction but slides laterally. Alternatively, the textured surface could be encapsulated with liquid that can solidify or cure (i.e., as an epoxy). Thus a curable liquid encapsulated surface could be as convenient to apply as a conventional tape, but have the strength of epoxy.

In some embodiments, the liquid-impregnated surface coating may be applied to condoms. The protective coating could allow for reduced friction during intercourse and could prevent tearing. Additionally, the surface coating could be applied to similar adult paraphernalia that is inserted into bodily orifices to reduce friction and minimize tearing.

In some embodiments, the liquid-impregnated surface coating may be applied to drug release patches. This product might appear similar to a Band-aid, but the white portion of the Band-aid would be replaced with a liquid encapsulated surface. The encapsulated liquid can be medication or drug. It can then be applied to the skin to deliver the medication.

In some embodiments, the liquid-impregnated surface coating may be applied to cosmetic products such as nail polish, shampoo, conditioner, body wash, hair gel, facemasks, and toothpaste. Applying such a coating to these cosmetic products allows them to repel dust and prevents dust that would otherwise be attracted to them to be applied to the body.

EXPERIMENTAL EXAMPLES

Example 1

FIG. 2 shows experimental measurements of blood droplet repulsion from tweezers coated with the liquid-impregnated surface coating. As shown in FIG. 2A, two identical plastic tweezers, tweezer 202 and tweezer 204 are dipped into container 206 which is filled with two drams of pig blood. Tweezer 202 is uncoated as a control tweezer. Tweezer 204 is coated with the liquid-impregnated surface coating. Tweezers 202 and 204 are dipped into container 206 at the same time and removed at the same time. Tweezers 202 and 204 are held in the same hand.

FIG. 2B shows the effect of the surface coating on tweezer 204 when both tweezers 202 and 204 are removed from container 206 of pig blood. The uncoated tweezer 202 is stained with blood residue. The liquid-impregnated surface coated tweezer 204 shed the majority of the blood away with minimal reside as soon as tweezer 204 was withdrawn from container 204.

The experiment of FIG. 2 demonstrates that liquid-impregnated surfaces can be engineered to keep medical devices clean of bodily fluids. This is helpful in keeping medical equipment and surgical tools sterile.

Example 2

This example demonstrates liquid-impregnated surface pills are easier to swallow than uncoated pills. It demonstrates this by comparing the sliding speed of a liquid-impregnated surface coated pill on a piece of steak against the sliding speed of an uncoated pill.

FIG. 3A shows a screenshot of a video taken to document coated pill 302 and uncoated pill 304 sliding on steak to mimic the esophagus and tongue tissue. The coated and uncoated pills were placed in a parallel orientation on two pieces of steak, steak 306 and 308 as show in FIG. 3A. Steak 306 and 308 were placed on an incline of 65°. Pill 302 was coated with a liquid impregnated surface (carnauba wax and ethyl oleate) whereas pill 304 was uncoated as a control.

In particular, tweezers were used to pick up the cylindrical pale yellow pills (Vitacost Alpha Lipoic Acid & Acetyl L-Carnitine HCl—1600 mg per serving). Carnauba wax was sprayed onto pill 302 for three seconds to apply uniform coating of the liquid-impregnated coating. Nitrogen gas was blown across pill 302 to allow time to dry coating prior to application of ethyl oleate. Ethyl oleate was sprayed onto pill 302 for three seconds to apply uniform coating. Subsequently, uncoated pill 304 was placed onto steak 308. Liquid-impregnated surface coated pill 302 was placed onto steak 306. Pills 302 and 304 were placed at top of their respective steak. The orientation of the pills was perpendicular to ruler 310. Subsequently, steaks 306 and 308 were adjusted to a 65 degree inclined plane. FIG. 3A shows pills 302 and 304 at zero seconds as soon as they were placed on the top of the steaks.

FIG. 3B shows a screenshot 3.5 seconds after pills 302 and 304 were placed on the top of the steaks. At this time, coated pill 302 reached the bottom of steak 306 while uncoated pill 304 remained at the top of steak 308. Pill 302 started sliding slowly but rapidly accelerated to a rate of ~4.5 cm/s (calculated based on a travel distance of 7 cm over 1.5 seconds. The uncoated pill remained at the top of the steak throughout the experiment.

The experiment of FIG. 3 demonstrates that liquid-impregnated surface coatings on pills helps the pill slide on top of animal tissue such as steak which mimics the surface structure of the human tongue and esophagus since the uncoated pill did not travel any distance on the steak at the same inclined angle.

Example 3

This example demonstrates the low friction between liquid-impregnated surfaces and flesh. This is demonstrated by comparing the sliding speed of raw eye round steak on a liquid impregnated surface with the sliding speed of another raw eye round steak on an uncoated surface. A video was taken was to document the steaks' motion on uncoated and coated polypropylene sheets.

This experiment was performed by first cutting a 12"×12" polypropylene (PP) sheet (Gauge=0.060") into two 6"×12" sheets, sheet 406 and 408. Carnauba wax was sprayed onto sheet 408 for fifteen to thirty second to apply uniform coating. Subsequently, ethyl oleate was sprayed onto sheet 408 for thirty to forty five second to apply uniform coating. Sheet 406 was left uncoated as control. Sheet 406 was placed next to sheet 408 and both sheets 406 and 408 were placed on a 45 degree incline. Steak 402 was placed on top of sheet 406 and steak 404 was placed on top of sheet 408. The beginning of the meat steaks were four inches from the top of the PP sheets. Video of the meat travelling was taken to document the difference between uncoated and coated PP sheets. FIG. 4A shows a video frame at time zero when the steaks were placed on top of the PP sheets. FIG. 4B shows a video frame one hundred and thirty one seconds after the frame shown in FIG. 4B. FIG. 4B shows that steak 404 has reached the bottom of sheet 408 while uncoated steak 402 still remains near the top of the PP sheet 406.

Time was measured for steak to travel eight inches to the bottom of the PP sheet. Steak 404 on PP sheet 408 took 131 seconds to travel to bottom of sheet. The average velocity of liquid-impregnated surface coated steak 404 on sheet 408 was 0.055 inches/sec. Uncoated steak 402 on PP sheet 406 slightly moved but remained about seven inches from the bottom of the sheet after 2 minutes and 30 seconds. Upon additional time (~5 mins), the steak did not appear to move any further down the inclined ramp.

The experiment of FIG. 4 demonstrates that liquid-impregnated surface coatings on surfaces helps animal flesh slide down the surface more easily than on uncoated surfaces. This provides evidence to prove that such a liquid-impregnated surface coating provides reduction of shear forces to prevent damage to cells and other biological structures in blood or other biological fluids being pumped.

Example 4

Figure 5A:
FIGS. 5A though 5D illustrate a mold-release experiment using concrete and a liquid-impregnated surface coated mold.
Figure 5B:

FIGS. 5A-D illustrate a mold-release experiment using concrete and a liquid-impregnated surface coated mold. In some embodiments, the liquid-impregnated surface coating may be applied to orthodontic tools such as a tooth mold. A heavily detailed plastic bottle in the shape of a monkey, complete with crevices and structures, was used to demonstrate liquid-impregnated surfaces as mold release/non-stick coatings as shown in FIG. 5A. The approximately 500 ml HDPE, monkey-shaped bottle was sawed in half with a reciprocating saw to create a front half and a back half as shown in FIG. 5B. The back half of the bottle was coated with a liquid impregnated surface, described below, while the front half remained uncoated.

A liquid impregnated solution was sprayed onto the back half of the bottle. The liquid-impregnated solution was prepared by using adding 1.5 g of fluorinated wax (HF diblock grey, Toko) to 80 ml of toluene and heated on a hot plate until total dissolving of the wax. Next, the solution was sonicated for 5 minutes and was let to cool down to room temperature. Finally 10 g of PTFE particles (1 μm size, Sigma) were added and sonicated for 5 minutes more. The solution was sprayed onto the mold to create a coating of approximately 10 um thickness, and then Galden HT 200 was sprayed to impregnate and fill the textures.

Figure 5C:
Figure 5D:
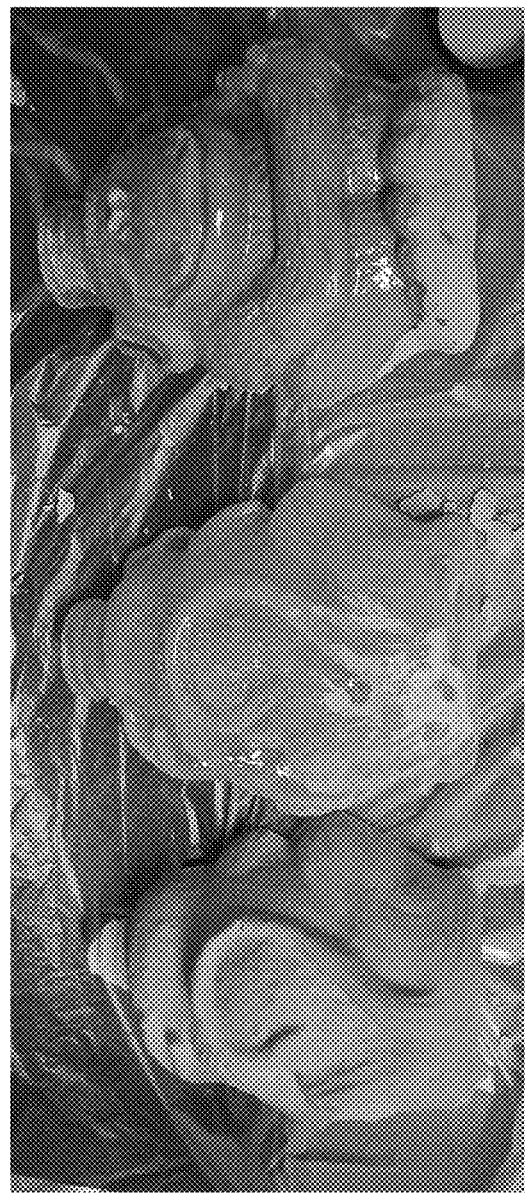

Rapid setting concrete was mixed per the manufacturer's instructions and poured into each mold until full as shown in FIG. 5C. The concrete was left to cure for approximately 15 minutes at room temperature (70° F.) and each mold was turned upside-down on the counter. We then pulled the coated plastic mold from the hardened concrete easily and completely, leaving behind a cast of the inside of the bottle as shown in FIG. 5D. The uncoated side would not release from the mold.

Example 5

Figure 6:
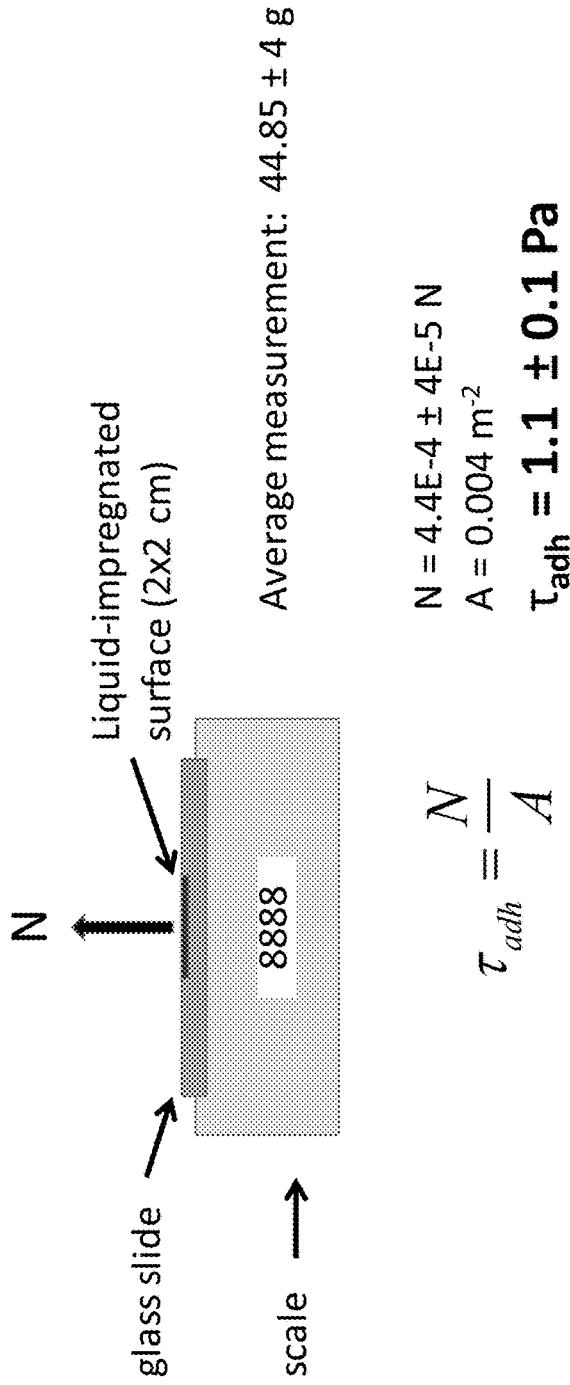
FIG. 6 illustrates a sold-to-solid adhesion experiment for determining the adhesion strength of liquid-impregnated surfaces.

FIG. 6 illustrates a solid-to-solid adhesion experiment. The lateral forces (sliding) depend on the impregnated liquid viscosity. An extremely high viscosity impregnated liquid can behave essentially as a solid, preventing sliding, and there for the surface would behave similarly to tape (FIG. 6). Low viscosity fluids slide easily, thus resulting in a surface that behave as an adhesive in the normal direction but slides laterally (Imagine an air hockey table where the mallets can easily slide but are extremely difficult to pull off).

The adhesion force was obtained by measuring the force needed to separate a liquid-impregnated surface from a glass slide in the normal direction. A glass slide was attached to the scale and the liquid-impregnated surface was pulled off of the surface in the normal direction. Capillarity forces due to the impregnated liquid resulted in adhesive strength of $\tau_{adh}=1.1\pm0.1$ Pa. The liquid-impregnated surface was prepared using a lithography patterned array of square posts of 10 um width and height, and spaced by 25 um. 10 cSt silicone oil was impregnated into the surface.

We measured the static coefficient of friction, $\mu_s$, between two solid materials with three different configurations. The first interface is silicon on PET (configuration 1), the second interface is silicon with the liquid impregnated surface (for which the normal adhesion was measured) on PET, and the third interface (configuration 3) is glass sprayed with carnauba wax to create a textured surface that was impregnated with ethyl oleate. The PET surface beneath was coated with a thin film of toothpaste to yield a chemistry that is preferentially contacted by ethyl oleate over the carnauba wax, insuring a stable liquid film between the solid materials. The coefficient of friction for each of these configuration was calculated as $\mu_s=\tan \alpha_{slide}$, where $\alpha_{slide}$ is the angle at which the surface first begins to slide. A weight was attached to the top of each surface resulting in a force per unit area of the top surface of around $520\pm10$ N/m$^2$ on each surface. The slide-off angles, $\alpha_{slide}$, for configuration 1, 2, and 3, were 24°, 16°, and 7° respectively resulting in coefficients of friction, $\mu_s=\tan \alpha_{slide}$ of 0.44, 0.29, and 0.12 respectively. Thus configurations 2 and 3 both produced lower coefficients of friction than the direct solid/solid interface (configuration 1) Configuration 3, for which the chemistry of the bottom was modified with a layer of toothpaste, had the lowest friction—presumably because the a thin film of liquid (ethyl oleate) is stable between toothpaste and the carnauba wax, and therefore there was no solid-to-solid contact.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A medical device or medical implement with high lubricity to flesh or biological fluid and/or inhibited nucleation on its surface, the device or implement comprising:
a surface comprising an impregnating liquid and a plurality of micro-scale and/or nano-scale solid features spaced sufficiently close to stably contain the impregnating liquid therebetween, wherein said impregnating liquid fills spaces between said solid features, wherein said surface stably contains said impregnating liquid between said solid features, wherein at least a portion of the micro-scale and/or nano-scale solid features are non-submerged by the impregnating liquid when the surface is in contact with the flesh or the biological fluid, and wherein said impregnating liquid is substantially held in place between said plurality of solid features regardless of orientation of said surface, wherein $0<\phi<0.3$, where $\phi$ is a surface area fraction of the surface non-submerged by said impregnating liquid, and wherein said surface is a textured surface and said solid features are engineered protrusions or engineered particles of said textured surface.

2. The medical device or medical implement of claim 1, wherein the solid features comprise particles having an average dimension in a range of 1 micron to 50 microns.

3. The medical device or medical implement of claim 1, wherein the particles are arranged with average spacing of about 1 micron to about 30 microns between adjacent particles or clusters of particles.

4. The medical device or medical implement of claim 1, wherein the particles are spray-deposited.

5. The medical device or medical implement of claim 1, wherein the impregnating liquid comprises at least one member selected from the group consisting of ethyl oleate, an ester, a fatty acid, a fatty acid derivative, a vegetable oil, a terpene, phenyl isothiocyanate, bromobenzene, iodobenzene, o-bromotoluene, alpha-chloronaphthalene, alpha-bromonaphthalene, acetylene tetrabromide, 1-butyl-3-methyl-imidazolium bis(trifluoromethylsulfonyl) imide, tribromohydrin, ethylene dibromide, carbon disulfide, bromoform, methylene iodide, stanolax, Squibb's liquid petrolatum, p-bromotoluene, monobromobenzene, perchloroethylene, carbon disulfide, phenyl mustard oil, monoiodobenzene, alpha-monochloro-naphthalene, acetylene tetrabromide, aniline, butyl alcohol, isoamyl alcohol, n-heptyl alcohol, cresol, oleic acid, linoleic acid, and amyl phthalate.

6. The medical device or medical implement of claim 1, wherein the solid features comprise one or more members selected from the group consisting of wax, carnauba wax, beeswax, candelilla wax, zein, dextrin, cellulose ether, hydroxyethyl cellulose, hydroxypropyl cellulose, hydroxyethyl methyl cellulose, hydroxypropyl methyl cellulose, ethyl hydroxyethyl cellulose, insoluble fiber, purified wood cellulose, micro-crystalline cellulose, kaolinite, Japan wax, pulp, ferric oxide, iron oxide, sodium formate, sodium oleate, sodium palmitate, sodium sulfate, a metal, a polymer, a ceramic solid, a fluorinated solid, an intermetallic solid, and a composite solid PDMS, cyclic olefin polymer, polypropylene, PVC, PET, HDPE, polyimide, PMMA, glass, Perspex, Plexiglass, and Polymacon.

7. The medical device or medical implement of claim 1, wherein the impregnating liquid comprises an additive to prevent or reduce evaporation of the impregnating liquid.

8. The medical device or medical implement of claim 1, wherein the medical device or medical implement is a member selected from the group consisting of braces, dentures, a retainer, orthodonture, a bridge, an implant, a tooth/teeth mold, a prosthesis, an artificial organ, an artificial artery, a stent, a syringe, a lining, an IV tube, an IV bag, a colostomy bag, a surgical instrument, a bandage, and a blood pump.

9. The medical device or medical implement of claim 1, wherein said medical device or medical implement is a blood pump or part thereof, wherein the surface is configured to provide reduction of shear forces to prevent damage to cells and/or other biological structures in blood or other biological fluids being pumped thereby or therethrough.

10. The medical device or medical implement of claim 1, wherein said medical device or medical implement is a member selected from the group consisting of a pill, capsule, tablet, gel cap, and suppository.

11. The medical device or medical implement of claim 1, wherein said medical device or medical implement is a member selected from the group consisting of a micropoipette, a small volume container of biological material, a human serum container, a pipette, a pipette tip, a microfluidic device, a dialysis machine, a tube, an endoscope, an intubation device, a syringe, a stent, a catheter, and a tracheotomy tube.

12. The medical device or medical implement of claim 1, wherein said medical device or medical implement is a member selected from the group consisting of a glove, bandage, adhesive strip, drug release patch, and condom.

13. The medical device or medical implement of claim 1, wherein said impregnating liquid comprises an antiseptic and/or an antibacterial.

14. The medical device or medical implement of claim 1, wherein said impregnating liquid is curable and can be converted to a solid by curing.

15. The medical device or medical implement of claim 1, wherein one or both of the following holds:
(i) $0<\phi<0.25$, where $\phi$ is a surface area fraction of the surface non-submerged by said impregnating liquid, and wherein said surface is a textured surface and said solid features are engineered protrusions or engineered particles of said textured surface; and
(ii) $S_{ow(a)}<0$, where $S_{ow(a)}$ is spreading coefficient, defined as $\gamma_{wa}-\gamma_{wo}-\gamma_{oa}$, where $\gamma$ is the interfacial tension between the two phases designated by subscripts w, a, and o, where w is water, a is air, and a is the impregnating liquid.

16. The medical device or medical implement of claim 15, wherein $0<\phi\leq0.25$.

17. The medical device or medical implement of claim 15, wherein $0.01<\phi\leq0.25$.

18. The medical device or medical implement of claim 15, wherein $0.01<\phi\leq0.10$.

19. The medical device or medical implement of claim 15, wherein $S_{ow(a)}<0$.

20. The medical device or medical implement of claim 1, wherein one or both of the following holds:
(i) $\theta_{os(w),receding}=0$; and
(ii) $\theta_{os(a),receding}=0$ and $\theta_{os(w),receding}=0$,
where $\theta_{os(w),receding}$ is receding contact angle of the impregnating liquid (subscript 'o') on the surface (subscript 's') in the presence of water (subscript 'w'), and where $\theta_{os(a),receding}$ is receding contact angle of the impregnating liquid (subscript 'o') on the surface (subscript 's') in the presence of air (subscript 'a').

* * * * *